United States Patent
Rodrigues et al.

(10) Patent No.: US 10,370,327 B2
(45) Date of Patent: Aug. 6, 2019

(54) IONIC LIQUID FILMS WITH MULTIPLE FUNCTIONALITIES FOR SURFACE MODIFICATION OF BIOMEDICAL ALLOYS

(71) Applicants: BOARD OF REGENTS, THE UNIVERSITY OF TEXAS SYSTEM, Austin, TX (US); UNIVERSIDADE FEDERAL DE SANTA MARIA, Santa Maria (BR)

(72) Inventors: Danieli C. Rodrigues, Richardson, TX (US); Izabelle de Mello Gindri, Dallas, TX (US); Clarissa P. Frizzo, Santa Maria (BR); Marcos A. P. Martins, Santa Maria (BR)

(73) Assignees: Board of Regents, The University of Texas System, Austin, TX (US); Universidade Federal De Santa Maria, Santa Maria (BR)

( * ) Notice: Subject to any disclaimer, the term of this patent is extended or adjusted under 35 U.S.C. 154(b) by 0 days.

(21) Appl. No.: 15/323,218

(22) PCT Filed: Jul. 2, 2015

(86) PCT No.: PCT/US2015/039078
§ 371 (c)(1),
(2) Date: Dec. 30, 2016

(87) PCT Pub. No.: WO2016/004366
PCT Pub. Date: Jan. 7, 2016

(65) Prior Publication Data
US 2017/0137380 A1 May 18, 2017

Related U.S. Application Data

(60) Provisional application No. 62/020,197, filed on Jul. 2, 2014.

(51) Int. Cl.
| | | |
|---|---|---|
| C07D 233/56 | (2006.01) | |
| C07D 403/06 | (2006.01) | |
| A61L 27/28 | (2006.01) | |
| C07D 207/44 | (2006.01) | |
| C07D 233/54 | (2006.01) | |
| A61C 8/02 | (2006.01) | |
| A61C 8/00 | (2006.01) | |
| A61L 27/06 | (2006.01) | |
| A61L 27/22 | (2006.01) | |
| A61L 27/54 | (2006.01) | |
| C07C 229/06 | (2006.01) | |
| C07C 229/36 | (2006.01) | |
| C07C 323/58 | (2006.01) | |
| C07C 333/12 | (2006.01) | |
| C07D 233/64 | (2006.01) | |
| C07H 3/02 | (2006.01) | |

(52) U.S. Cl.
CPC .......... *C07D 207/44* (2013.01); *A61C 8/0006* (2013.01); *A61C 8/0015* (2013.01); *A61L 27/06* (2013.01); *A61L 27/227* (2013.01); *A61L 27/28* (2013.01); *A61L 27/54* (2013.01); *C07C 229/06* (2013.01); *C07C 229/36* (2013.01); *C07C 323/58* (2013.01); *C07C 333/12* (2013.01); *C07D 233/54* (2013.01); *C07D 233/64* (2013.01); *C07D 403/06* (2013.01); *C07H 3/02* (2013.01); *A61L 2300/204* (2013.01); *A61L 2300/21* (2013.01); *A61L 2300/232* (2013.01); *A61L 2300/404* (2013.01); *A61L 2400/18* (2013.01); *A61L 2420/06* (2013.01); *A61L 2430/02* (2013.01); *A61L 2430/34* (2013.01)

(58) Field of Classification Search
None
See application file for complete search history.

(56) References Cited

U.S. PATENT DOCUMENTS

| | | | |
|---|---|---|---|
| 6,039,568 A | 3/2000 | Hinds | |
| 8,075,312 B2 | 12/2011 | Collins | |
| 2005/0037319 A1 | 2/2005 | Bulard | |
| 2010/0154889 A1* | 6/2010 | Tung | C07D 233/58 136/261 |
| 2012/0077151 A1 | 3/2012 | Filho | |
| 2012/0276503 A1 | 11/2012 | Wang et al. | |
| 2013/0040439 A1 | 2/2013 | Zhao et al. | |
| 2013/0337027 A1 | 12/2013 | Smith et al. | |
| 2013/0337037 A1 | 12/2013 | Finkielsztein | |
| 2015/0174145 A1 | 6/2015 | Correia | |

OTHER PUBLICATIONS

Shirota, Hideaki, et al. "Comparison between dicationic and monocationic ionic liquids: liquid density, thermal properties, surface tension, and shear viscosity." Journal of Chemical & Engineering Data 56.5 (2011): 2453-2459 and supporting information (Year: 2011).*
Zhang, Yi, Ping Yu, and Yunbai Luo. "Absorption of CO2 by amino acid-functionalized and traditional dicationic ionic liquids: Properties, Henry's law constants and mechanisms." Chemical engineering journal 214 (2013): 355-363. (Year: 2013).*
Zhang, Yanqiang, et al. "Dual amino-functionalised phosphonium ionic liquids for CO2 capture." Chemistry—A European Journal 15.12 (2009): 3003-3011. (Year: 2009).*
Albertini et al., "Assessment of periodontal and opportunistic flora in patients with peri-implantitis." *Clinical oral implants research* 26.8 (2015): 937-941.
Bermúdez, María-Dolores, et al. "Ionic liquids as advanced lubricant fluids." *Molecules* 14.8 (2009): 2888-2908.

(Continued)

*Primary Examiner* — Nissa M Westerberg
(74) *Attorney, Agent, or Firm* — Parker Highlander PLLC

(57) ABSTRACT

The present disclosure relates ionic liquids which are used as lubricants for medical devices. In some aspects, the ionic liquids of the present disclosure can exhibit antimicrobial or host cell integrative activity or a combination of functionalities. In some aspects, the present disclosure also provides devices coated with the ionic liquid.

12 Claims, 8 Drawing Sheets

(56) References Cited

OTHER PUBLICATIONS

Bernot, Randall J., et al, "Acute and chronic toxicity of imidazolium-based ionic liquids on Daphnia magna." *Environmental Toxicology and Chemistry* 24.1 (2005): 87-92.

Casal-Dujat et al., Gemini imidazolium amphiphiles for the synthesis, stabilization, and drug delivery from goldnNanoparticles. Langmiur 2012; 28:2368-2381.

Cheng, Han-Yi, et al, "Stress effect on bone remodeling and osseointegration on dental implant with novel nano/microporous surface functionalization." *Journal of Biomedical Materials Research Part A* 101.4 (2013): 1158-1164.

Chin, Mervyn YH, et al. "Biofilm formation on surface characterized micro-implants for skeletal anchorage in orthodontics." *Biomaterials* 28.11 (2007): 2032-2040.

Cvjetko, Marina, et al. "Cytotoxic effects of imidazolium ionic liquids on fish and human cell lines." *Archives of Industrial Hygiene and Toxicology* 63.1 (2012): 15-20.

Dahléh Gunnar, et al. "Virulence factors and antibiotic susceptibility in enterococci isolated from oral mucosal and deep infections." *Journal of oral microbiology* 4.1 (2012): 10855.

Ferris, D. M., et al. "RGD-coated titanium implants stimulate increased bone formation in vivo." *Biomaterials* 20.23 (1999): 2323-2331.

Frizzo et al., Pharmaceutical salts: solids to liquids by using ionic liquid design. Pharmaceutical Salts: Solids to Liquids by Using Ionic Liquid Design. 1 ed.: Intech, v.1 , p. 557-579, 2013.

Fukumoto, Kenta, Masahiro Yoshizawa, and Hiroyuki Ohno. "Room temperature ionic liquids from 20 natural amino acids," *Journal of the American Chemical Society* 127.8 (2005): 2398-2399.

Garcia et al., Biodegradable ionic liquids. Part II. Effect of the anion and toxicology. Green Chemistry 2005; 7:9-14.

Garcia-Lorenzo, Andrés, et al. "Cytotoxicity of selected imidazolium-derived ionic liquids in the human Caco-2 cell line. Sub-structural toxicological interpretation through a QSAR study." *Green chemistry* 10.5 (2008): 508-516.

Gibson, P.N., Stamm, H. The Use of Alloys in Prosthetic Devices. Business Briefing: Medical Device Manufacturing & Technology 2002, Jun. 2002, 48-51, World Markets Research Centre Ltd. Publs.

Gindri et al. "Dicationic imidazolium-based ionic liquids: a new strategy for non-toxic and antimicrobial materials." RSC Advances 4.107 (2014): 62594-62602.

Gindri, Izabelle M., et al. "Ionic liquid coatings for titanium surfaces: effect of IL structure on coating profile," *ACS applied materials & interfaces* 7.49 (2015): 27421-27431.

Gindri, Izabelle M., et al. "Preparation of TiO2 nanoparticies coated with ionic liquids: a supramolecular approach." *ACS applied materials & interfaces* 6.14 (2014): 11536-11543.

Goldberg, Jay R., and Jeremy L. Gilbert. "The electrochemical and mechanical behavior of passivated and TiN/AlN-coated CoCrMo and Ti6Al4V alloys." *Biomaterials* 25.5 (2004): 851-864.

Hendry, Jason A., and Robert M. Pilliar, "The fretting corrosion resistance of PVD surface-modified orthopedic implant alloys." *Journal of Biomedical Materials Research Part A* 58.2 (2001): 156-166.

Holmberg, Kyle V., et al. "Bio-inspired stable antimicrobial peptide coatings for dental applications." *Acta biomaterialia* 9.9 (2013): 8224-8231.

International Preliminary Report on Patentability issued in International Application No. PCT/US2015/039078, dated Jan. 12, 2017.

International Search Report and Written Opinion issued in International Application No. PCT/US2015/039078, dated Nov. 25, 2015.

Invitation to Pay Additional Fees issued in International Application No. PCT/US2015/039078, dated Sep. 11, 2015.

Jiménez, A. E., and M. D. Bermúdez. "Ionic liquids as lubricants of titanium-steel contact. Part 3. Ti6Al4V lubricated with imidazolium ionic liquids with different alkyl chain lengths," *Tribology letters* 40.2 (2010): 237-246.

Jiménez, Ana Eva, and Maria-Dolores Bermúdez. "Ionic liquids as lubricants of titanium-steel contact." *Tribology letters* 33.2 (2009): 111-126.

Kazemzadeh-Narhat, Mehdi, et al. "Drug release and bone growth studies of antimicrobial peptide-loaded calcium phosphate coating on titanium." *Journal of Biomedical Materials Research Part B: Applied Biomaterials* 100.5 (2012): 1344-1352.

Kumar, Mukesh, et al. "Effect of glycidyl methacrylate (GMA) on the thermal, mechanical and morphological property of biodegradable PLA/PBAT blend and its nanocomposites." *Bioresource technology* 101.21 (2010): 8406-8415.

Liu, Weimin, et al. "Tribological performance of room-temperature ionic liquids as lubricant." *Tribology Letters* 13.2 (2002): 81-85.

Minami, Ichiro. "Ionic liquids in tribology," *Molecules* 14.6 (2009): 2286-2305.

Moniruzzaman et al. Ionic liquid based microemulsion with pharmaceutically accepted components: formulation and potential applications. Journal of Colloid and Interface Science 2010; 353:136-142.

Nováková, Dana, et al. "Evaluation of the strain identity between isolates from caries lesions and root canals in early childhood caries cases." *Folia microbiologica* 58.6 (2013): 649-656.

Palacio, Manuel, and Bharat Bhushan. "Ultrathin Wear-Resistant Ionic Liquid Films for Novel MEMS/NEMS Applications." *Advanced Materials* 20.6 (2008): 1194-1198.

Pemak et al. Phosphonium acesulfamate based ionic liquids. European Journal of Organic Chemistry 2005; 4:650-652.

PubChem SID: 143759042, "ST51001410", dated Aug. 29, 2012.

Radošević, Kristina, et al. "In vitro cytotoxicity assessment of imidazolium ionic liquids: biological effects in fish Channel Catfish Ovary (CCO) cell line," *Ecotoxicology and environmental safety* 92 (201:3): 112-118.

Rodrigues et al. Titanium corrosion mechanisms in the oral environment: a retrieval study. Accepted for publication in the Journal Materials. Oct. 2013.

Romero, A., et al. "Toxicity and biodegradability of imidazolium ionic liquids." *Journal of Hazardous Materials* 151.1 (2008): 268-273.

Sánchez, M. C., et al. "An in vitro biofilm model associated to dental implants: Structural and quantitative analysis of in vitro biofilm formation on different dental implant surfaces," *Dental Materials* 30.10 (2014): 1161-1171.

Shang, Zhen-Zhen, et al. "Differentially expressed genes and signalling pathways are involved in mouse osteoblast-like MC3T3-E1 cells exposed to 17-β estradiol." *International Journal of Oral Science* 6.3 (2014): 142.

Sievert, Dawn M., et al. "Antimicrobial-resistant pathogens associated with healthcare-associated infections summary of data reported to the National Healthcare Safety Network at the Centers for Disease Control and Prevention, 2009-2010." *Infection Control & Hospital Epidemiology* 34.1 (2013): 1-14.

Simchi, A., et al. "Recent progress in inorganic and composite coatings with bactericidal capability for orthopaedic applications." *Nanomedicine: Nanotechnology, Biology and Medicine* 7.1 (2011): 22-39.

Svensson, Sara, et al. "Osseointegration of titanium with an antimicrobial nanostructured noble metal coating," *Nanomedicine: Nanotechnology, Biology and Medicine* 9.7 (2013): 1048-4056.

Torres et al. "Quaternary Salts of 1, 2-Bisazolyl-and 1, 2-Bisbenzazolylethanes." Bulletin des Sociétés Chimiques Belges 101.1 (1992): 29-35.

Tsuchiya, Hiroyuki, et al. "Innovative antimicrobial coating of titanium implants with iodine." *Journal of Orthopaedic Science* 17.5 (2012): 595-604.

Tsui et al., "Plasma sprayed hydroxyapatite coatings on titanium substrates Part 1: Mechanical properties and residual stress levels." *Biomaterials* 19.22 (1998): 2015-2029.

Tsui, et al. "Plasma sprayed hydroxyapatite coatings on titanium substrates Part 2: optimisation of coating properties." *Biomaterials* 19.22 (1998): 2031-2043.

Vallee et al., "Peptide interactions with metal and oxide sufaces", *Accounts of Chemical Research*9, 43(10):1297-1306, 2012.

(56) References Cited

OTHER PUBLICATIONS

Vargas-Reus, Miguel A., et al. "Antimicrobial activity of nanoparticulate metal oxides against peri-implantitis pathogens." *International journal of antimicrobial agents* 40.2 (2012): 135-139.

Wang, Bing, et al. "Proliferation and differentiation of osteoblastic cells on silicon-doped TiO 2 film deposited by cathodic arc," *Biomedicine & Pharmacotherapy* 66.8 (2012): 633-641.

Wang, Wilson, Youheng Ouyang, and Chye Khoon Poh. "Orthopaedic implant technology: biomaterials from past to future." *Annals of the Academy of Medicine-Singapore* 40.5 (2011): 237-244.

Wilson Jr, Thomas G., et al. "Foreign bodies associated with peri-implantitis human biopsies." *Journal of periodontology* 86.1 (2015): 9-15.

Wittmar, Alexandra, and Mathias Ulbricht. "Dispersions of various titania nanoparticles in two different ionic liquids." *Industrial & Engineering Chemistry Research* 51.25 (2012): 8425-8433.

Yu Bo et al. Tribological properties of ultra-thin ionic liquid films on single-crystal silicon wafers with functionalized surfaces. Tribology International 2006; 39:879-887.

Yu G. et al. Preparation of functional ionic liquids and tribological investigation of their ultra-thin films. Wear 2006; 260:1076-1080.

Zhao W. et al. Effect of cation on micro/nano-tribological properties of ultra-thin ionic liquid films. Tribology International 2009; 42:828-835.

Zhao, Bingran, et al. "Soft tissue integration versus early biofilm formation on different dental implant materials." *Dental materials* 30.7 (2014): 716-727.

Zhou, Feng, Yongmin Liang, and Weimin Liu. "Ionic liquid lubricants: designed chemistry for engineering applications." *Chemical Society Reviews* 38.9 (2009): 2590-2599.

Zhu et al. Effect of the anion on the tribological properties of ionic liquid nano-films on surface-modified silicon wafers. Tribology Letters 2008; 29:177-183.

* cited by examiner

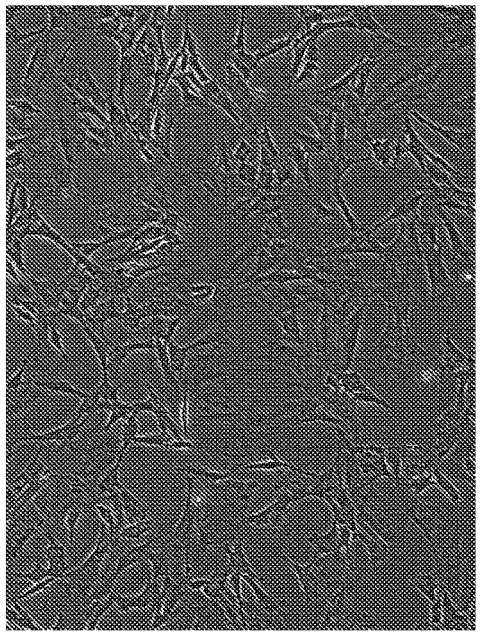
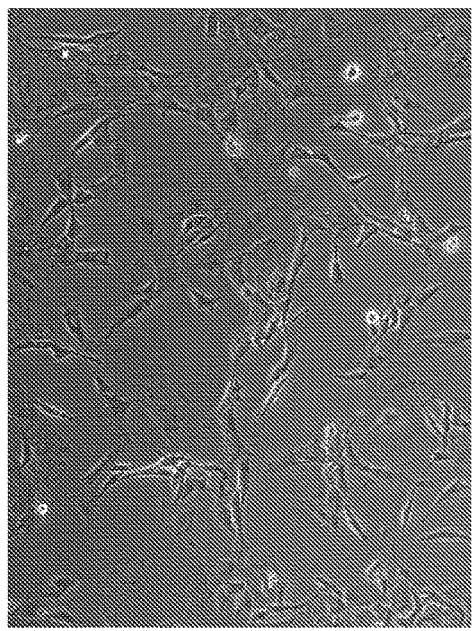
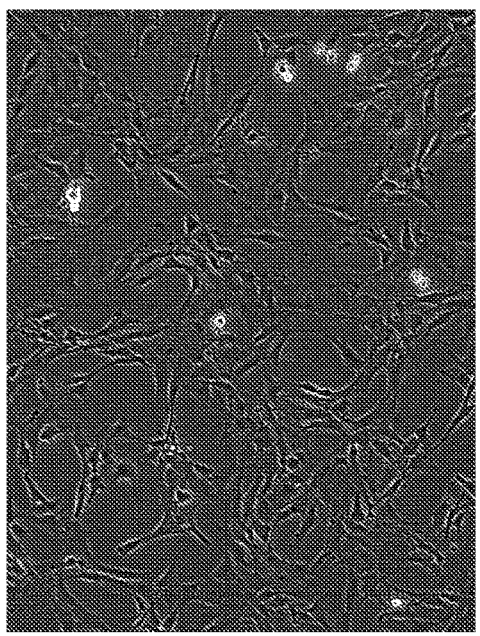
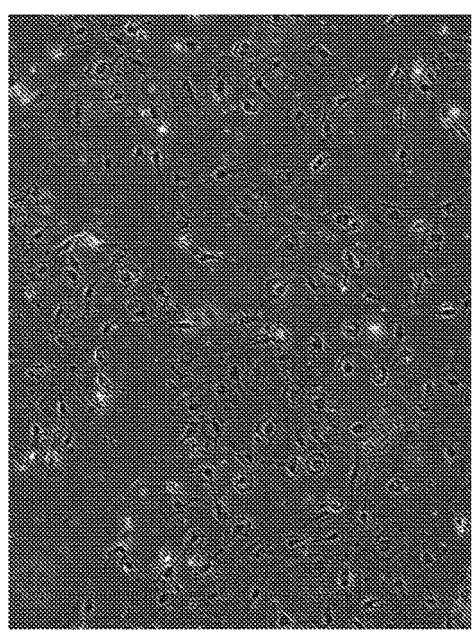
FIGS. 5A-D

IONIC LIQUID FILMS WITH MULTIPLE FUNCTIONALITIES FOR SURFACE MODIFICATION OF BIOMEDICAL ALLOYS

This application is a national phase application under 35 U.S.C. § 371 of International Application No. PCT/US2015/039078, filed Jul. 2, 2015, which claims the benefit of priority to U.S. Provisional Application Ser. No. 62/020,197, filed on Jul. 2, 2014, the entire contents of both are incorporated herein by reference.

BACKGROUND OF THE INVENTION

1. Field of the Invention

The present disclosure relates generally to the fields of ionic liquids, lubricant compounds, osseointegrative compounds, antimicrobial compounds, biomedical alloys, and surface modification. In particular, the disclosure relates to ionic liquids which can be deposited on devices.

2. Description of Related Art

Titanium and its alloys are broadly used in the design of dental and orthopedic implants due to a combination of attractive properties that include high corrosion resistance, biocompatibility, passivation and adequate mechanical properties. However, orthopedic implants are normally subject to wear and friction because they lack the body natural lubrication, which keeps joints immune to wear (Streicher, 1998). Modular implants designed with metal-on-metal (MoM) connections are rather popular in orthopedic and oral prostheses nowadays given their flexibility for matching patient anatomy and ease of intraoperative adjustments. However, such MoM modular connections are prone to micromotion and have been reported to wear and undergo corrosion in the absence of lubrication. This phenomenon, known as fretting-crevice corrosion, will ultimately lead to exposure of the bulk metal to active dissolution. Dissolution and consequent leaching of metal ions and debris in vivo can trigger inflammatory responses and adverse tissue reactions. Retrieval studies have shown several cases of implant failure as a consequence of the conjoint effects of corrosion and fretting (Gilbert et al., 1993; Gilbert et al., 1997; Jacobs et al., 1998; Goldberg et al., 2002). Collier et al. (1991) found that 17 of 30 mixed-metal femoral prostheses presented time dependent evidence of corrosion, in which the crevice provided between the head and neck connection functioned as corrosion sites due to the development of stagnant aqueous environments at those interfaces. The use of MoM in the articulation interfaces between the acetabular cup and femoral head of hip implants has been recently decreased due to reports of high failure rates and adverse local tissue reaction including pseudotumors and peri-fluid collections. Modularity in other implant areas such as the head-neck, stem-stem and stem-neck are also sources of corrosion and wear (Rodrigues et al. 2009). Corrosion has also been observed with titanium dental implants, and has been suggested to be one of triggering factors for peri-implantitis. Current designs of dental implants containing a modular abutment and smooth collar are also subject to corrosion because those areas are highly exposed to the oral environment, which can become acidic in the event of inflammation or presence of bacterial biofilms (Rodrigues et al., 2013). Bacterial biofilms can get adhered to the surface of a dental implant interrupting the process of osseointegration, which can lead to implant loosening and failure. These observations show that implant modularity can lead to corrosion. The presence of bacteria in the oral environment, for example, can lead to a significant reduction of the environment pH, which can trigger surface corrosion. Besides providing the conditions to trigger oxidation, bacterial biofilms can get adhered to the surface of implants interrupting surface aeration and leading to the permanent breakdown of the oxide layer, which will disrupt integration of the implant with bone.

Titanium and its alloys (Ti) form an oxide layer in presence of oxygen that will ensure bioactivity and protection against corrosion. Because the bioactivity of Ti oxides is not sufficient to provide anchorage of an implant, several strategies have been developed to modify the surface of the material to achieve integration with bone (Wang et al., 2011). Osseointegration is an important step to ensure implant success; this is especially important with dental implants. When the surface of a dental implant is well-integrated, it will provide mechanical stability and prevent entrance/leakage of bacteria (Svensson et al., 2013). It has been discussed in the literature that biofilm adhesion on the surface of dental implants and/or mechanical overload can hinder osseointegration and cause implant loosening (Renvert et al., 2007; Simchi et al., 2011; Zemmerli et al., 2006; Davis, 2003; Tillander et al., 2010; Quirynen et al., 1993; Quirynen et al., 2002). The scenario is similar with orthopedic implants, where the more porous exterior surfaces will achieve better integration.

Concerns related to infection with dental and orthopedic implants have led many researchers to explore coatings that can deliver antimicrobial/antibiotic compounds (Simchi et al., 2011; Svensson et al., 2013; Tsuchiya et al., 2012; Holmberg et al., 2013; Vargas-Reus et al., 2012; Cheng et al., 2013; Narbat et al., 2012) against biofilm adhesion. Thus, osseointegrative and antimicrobial activity are desirable surface characteristics. Surface modification of implants performed via chemical, physical and electro-chemical approaches have produced diverging results. Surface macro- and micro-texturing achieved by methods such as grit-blasting, plasma spraying, sintered beads, fiber meshes have been reported to produce heterogeneous coatings, degradation, delamination and particle release over time (Wang et al., 2011, Ferris et al., 1999; Gibson and Stamn, 2012). Current antimicrobial coatings prepared using specific chemistries such as silver, iodine, organosilane compounds and nitric oxide, have produced inconsistent results (Simchi et al., 2011; Tsuchiya et al., 2012).

Given the current trend with implant designs, novel methods for surface protection of implant contacting interfaces are of great importance. Typical surface treatments are not applicable to the irregular modular areas of orthopedic implants because they alter surface roughness or do not promote the formation of homogenous layers on the substrate. These rough coatings have also been reported to fail releasing fragments in the body. Ionic liquids (ILs) are currently under investigation as lubricant for applications where conventional oils and other lubricants are not applicable. Jimenez and Bermudez (2009) have studied the use of ILs as lubricants of high temperature metals and alloys such as titanium and nickel. Ionic liquids are molten salts, which possesses a combination of excellent properties such as non-volatility, non-flammability, thermo-oxidative stability, high ionic conductivity, wide electrochemical window, and miscibility with organic compounds (Bermudez et al., 2009; Minami, 2009; Liu et al., 2002). They were demonstrated to have good lubrication and wear resistant properties for materials that slide against each other, as in the case of steel-steel and titanium-steel counterparts (Jimenez and Bermudez, 2009). ILs are usually composed of an organic cation, typically containing nitrogen or phosphorous, and a weekly coordinating anion. Some of the most common cations employed are imidazolium, phosphonium, pyridinium and ammonium, while some common anions are $BF_4^-$, $PF_6^-$, $CF_3SO_3^-$ and $N(CF_3SO_2)_2^-$ (Bermudez et al., 2009). The anions have a significant influence on the tribological properties of ILs, for example, anionic moieties should be hydrophobic to improve substrate-IL properties. When there is formation of complexes between substrates and IL molecules, adsorbed IL layers become stable protecting the surface (Bermudez et al., 2009). The excellent tribological properties of IL additives are attributed to the formation of physically adsorbed films on different substrates.

Because of the need for improved lubrication of implant modular connections, protection of the surface against biofilm formation, while providing a permissive environment for host cell integration (soft and hard tissue integration) for successful implant fixation, the development of new surface modification techniques is of importance. This disclosure provides new multifunctional ionic liquids which in some aspects can be used for surface modification of biomedical implants.

SUMMARY OF THE INVENTION

Thus, in accordance with the present disclosure, there is provided an ionic liquid comprising (a) a cation of the formula:

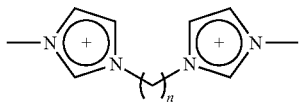

(I)

wherein: n is 2-16; or a cation of the formula:

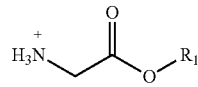

(II)

wherein: $R_1$ is alkyl$_{(C\leq12)}$, cycloalkyl$_{(C\leq12)}$, alkenyl$_{(C\leq12)}$, cycloalkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any one of these groups; and (b) an anion selected from a β-lactam compound, an amino acid$_{(C\leq18)}$; phosphate, alkylphosphate$_{(C\leq12)}$, substituted alkylphosphate$_{(C\leq12)}$, dialkylphosphate$_{(C\leq12)}$, substituted dialkylphosphate$_{(C\leq12)}$, sugar, ascorbic acid, $B(Y_1)(Y_2)(Y_3)(Y_4)^-$, wherein $Y_1$, $Y_2$, $Y_3$, and $Y_4$ are each independently selected from halogen; hydroxyl; amino; alkyl$_{(C\leq6)}$; alkenyl$_{(C\leq6)}$; alkynyl$_{(C\leq6)}$; aryl$_{(C\leq12)}$; aralkyl$_{(C\leq12)}$; acyl$_{(C\leq6)}$; alkoxy$_{(C\leq6)}$; aryloxy$_{(C\leq12)}$; acyloxy$_{(C\leq6)}$; or a substituted version of any of the last nine groups, halogen, and $N(A_1)(A_2)^-$ wherein: $A_1$ and $A_2$ are each independently selected from alkyl$_{(C\leq12)}$, substituted alkyl$_{(C\leq12)}$, cycloalkyl$_{(C\leq12)}$, substituted cycloalkyl$_{(C\leq12)}$, alkylsulfonyl$_{(C\leq12)}$, substituted alkylsulfonyl$_{(C\leq12)}$, cycloalkylsulfonyl$_{(C\leq12)}$, or substituted cycloalkylsulfonyl$_{(C\leq12)}$; provided that when the cation has formula I, then the anion is not tetravalent boron compound$_{(C\leq18)}$, substituted tetravalent boron compound$_{(C\leq18)}$, halogen, and $N(A_1)(A_2)^-$, wherein $A_1$ and $A_2$ are each independently selected from alkyl$_{(C\leq12)}$, substituted alkyl$_{(C\leq12)}$, alkylsulfonyl$_{(C\leq12)}$, or substituted alkylsulfonyl$_{(C\leq12)}$. In some embodiments, the cation is of formula I. In some embodiments, n is 4, 5, 6, 7, 8, 9, 10, 11, 12, 13, or 14. In some embodiments, n is 6, 7, 8, 9, 10, 11, or 12. In some embodiments, n is 8 or 10. In some embodiments, the cation is further defined by the formula:

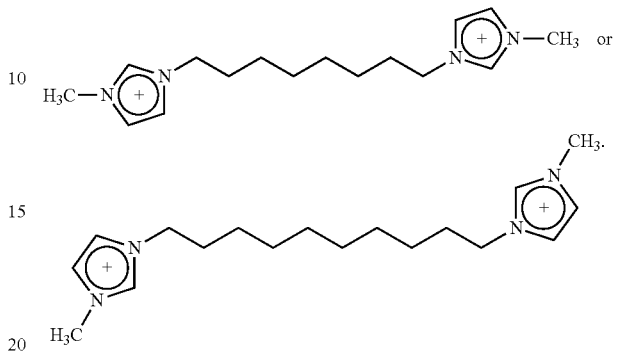

In other embodiments, the cation is of formula II. In some embodiments, $R_1$ is alkyl$_{(C\leq12)}$ or substituted alkyl$_{(C\leq12)}$. In some embodiments, $R_1$ is alkyl$_{(C\leq8)}$ or substituted alkyl$_{(C\leq8)}$. In some embodiments, $R_1$ is alkyl$_{(C\leq8)}$. In some embodiments, $R_1$ is methyl. In some embodiments, the cation is further defined by the formula:

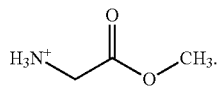

In some embodiments, the anion is an amino acid$_{(C\leq12)}$. In some embodiments, amino acid is an α-amino acid$_{(C\leq12)}$. In some embodiments, the α-amino acid$_{(C\leq12)}$ is selected from the 20 canonical amino acid. In some embodiments, the amino acid$_{(C\leq12)}$ is selected from:

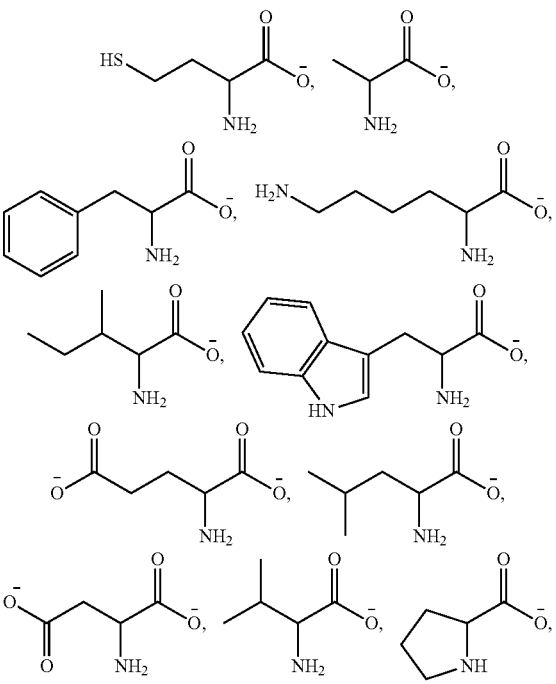

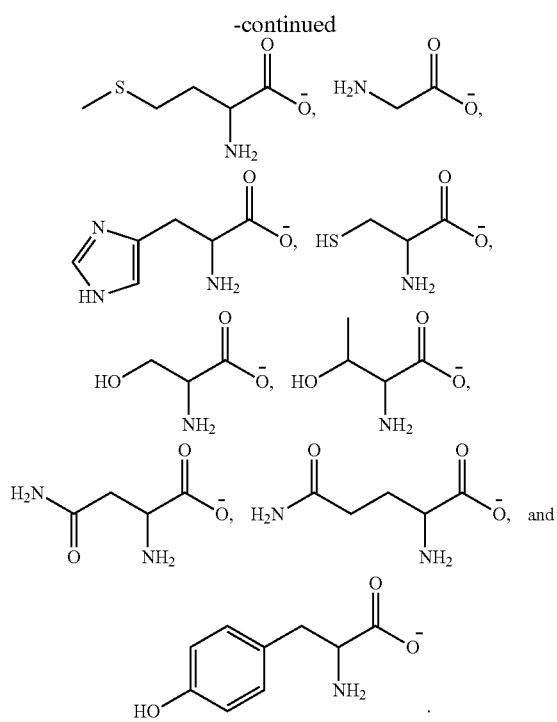

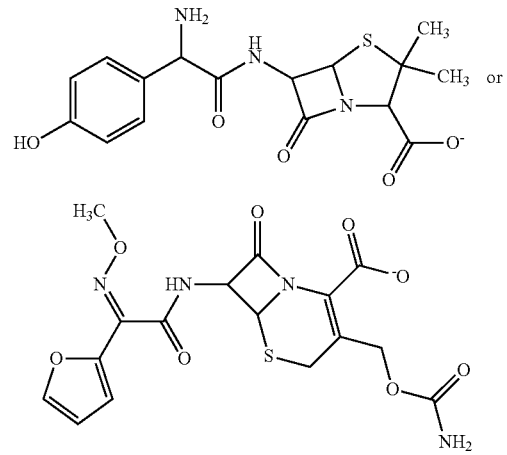

In other embodiments, the anion is phosphate. In other embodiments, the anion is $B(Y_1)(Y_2)(Y_3)(Y_4)^-$, wherein $Y_1$, $Y_2$, $Y_3$, and $Y_4$ are each independently selected from halogen, hydroxyl, amino, $alkyl_{(C\leq 6)}$, $alkenyl_{(C\leq 6)}$, $alkynyl_{(C\leq 6)}$, $aryl_{(C\leq 12)}$, $aralkyl_{(C\leq 12)}$, $acyl_{(C\leq 6)}$, $alkoxy_{(C\leq 6)}$, $aryloxy_{(C\leq 12)}$, $acyloxy_{(C\leq 6)}$, or a substituted version of any of these groups. In some embodiments, $Y_1$ is halogen. In some embodiments, $Y_2$ is halogen. In some embodiments, $Y_3$ is halogen. In some embodiments, $Y_4$ is halogen. In some embodiments, $Y_1$, $Y_2$, $Y_3$, or $Y_4$ is fluoride. In some embodiments, $Y_1$, $Y_2$, $Y_3$, and $Y_4$ are fluoride. In some embodiments, $B(Y_1)(Y_2)(Y_3)(Y_4)^-$ is $BF_4$. In other embodiments, the anion is a sugar. In other embodiments, the anion is ascorbic acid. In other embodiments, the anion is $N(A_1)(A_2)^-$. In some embodiments, $A_1$ is $alkylsulfonyl_{(C\leq 12)}$ or substituted $alkylsulfonyl_{(C\leq 12)}$. In some embodiments, $A_1$ is substituted $alkylsulfonyl_{(C\leq 12)}$. In some embodiments, $A_1$ is substituted $alkylsulfonyl_{(C\leq 8)}$. In some embodiments, $A_1$ is substituted $alkylsulfonyl_{(C\leq 6)}$. In some embodiments, the substituted $alkylsulfonyl_{(C\leq 6)}$ is $haloalkylsulfonyl_{(C\leq 6)}$. In some embodiments, the $haloalkylsulfonyl_{(C\leq 6)}$ is $fluoroalkylsulfonyl_{(C\leq 6)}$. In some embodiments, $A_1$ is trifluoromethylsulfonyl or pentafluoroethylsulfonyl. In some embodiments, $A_2$ is $alkylsulfonyl_{(C\leq 12)}$ or substituted $alkylsulfonyl_{(C\leq 12)}$. In some embodiments, $A_2$ is substituted $alkylsulfonyl_{(C\leq 12)}$. In some embodiments, $A_2$ is substituted $alkylsulfonyl_{(C\leq 8)}$. In some embodiments, $A_2$ is substituted $alkylsulfonyl_{(C\leq 6)}$. In some embodiments, the substituted $alkylsulfonyl_{(C\leq 6)}$ is $haloalkylsulfonyl_{(C\leq 6)}$. In some embodiments, the $haloalkylsulfonyl_{(C\leq 6)}$ is $fluoroalkylsulfonyl_{(C\leq 6)}$. In some embodiments, $A_2$ is trifluoromethylsulfonyl or pentafluoroethylsulfonyl. In some embodiments, the anion is di(trifluoromethylsulfonyl)amide or di(pentafluoroethylsulfonyl)amide. In other embodiments, the anion is a β-lactam compound. In some embodiments, the β-lactam compound is a β-lactam antibiotic. In some embodiments, the β-lactam antibiotic belonging to a class selected from penam, penem, cephem, monobactam, or carbapenem. In some embodiments, the β-lactam antibiotic class belongs to the penam class or the cephem class. In some embodiments, the β-lactam antibiotic further comprises a carboxylate group. In some embodiments, the β-lactam compound is amoxicillin or cefuroxime. In some embodiments, the antibiotic has the formula:

or a pharmaceutically acceptable salt thereof.

In yet another aspect, the present disclosure provides ionic liquids comprising:

(a) a cation of the formula:

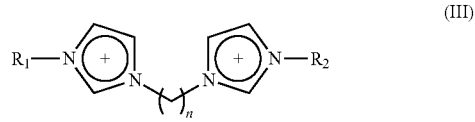

wherein: $R_1$ and $R_2$ are $alkyl_{(C\leq 8)}$ or substituted alkyl $_{(C\leq 12)}$; and n is 2-16; and (b) an anion selected from an amino $acid_{(C\leq 18)}$; sugar, and ascorbic acid.

In some embodiments, $R_1$ is methyl. In some embodiments, $R_2$ is methyl. In some embodiments, the cation is further defined by the formula:

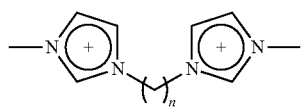

wherein: n is 2, 3, 4, 5, 6, 7, 8, 9, 10, 11, 12, 13, 14, 15, or 16. In some embodiments, the cation is:

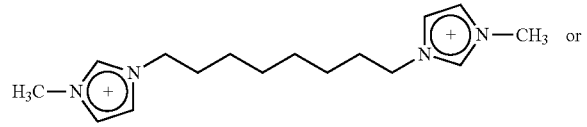

7
-continued
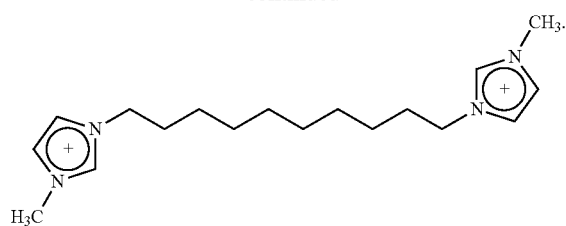
In some embodiments, the anion is an amino acid$_{(C \leq 18)}$. In some embodiments, the amino acid$_{(C \leq 18)}$ is:
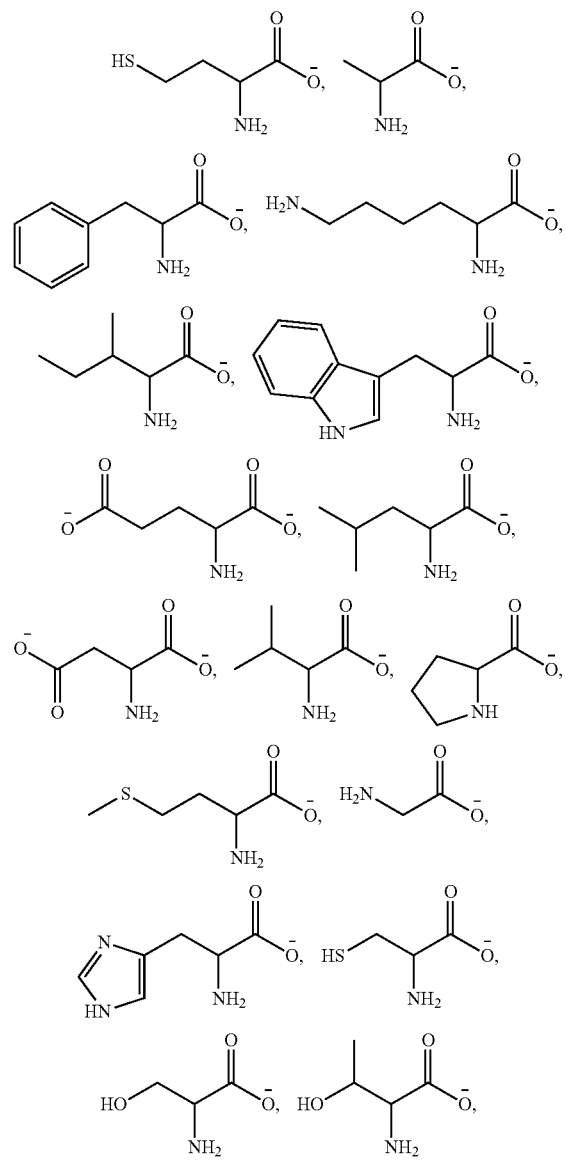
8
-continued
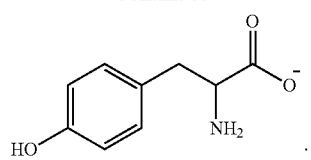
In some embodiments, the amino acid$_{(C \leq 18)}$ is:
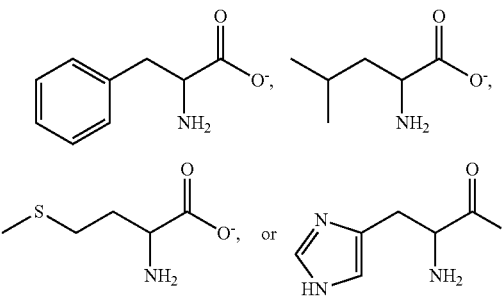
In other embodiments, the anion is an anion of ascorbic acid. In some embodiments, the ionic liquid is further defined as:
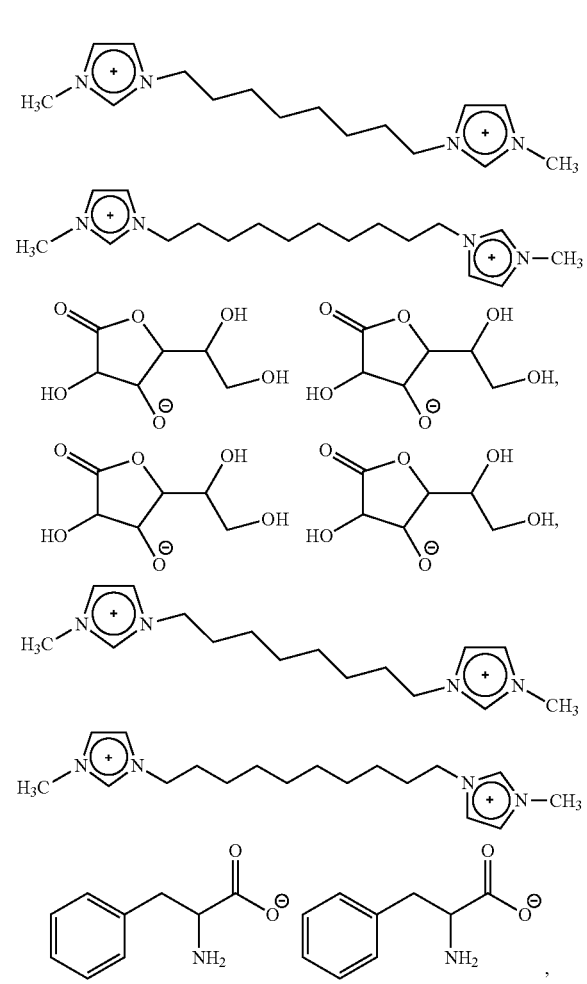

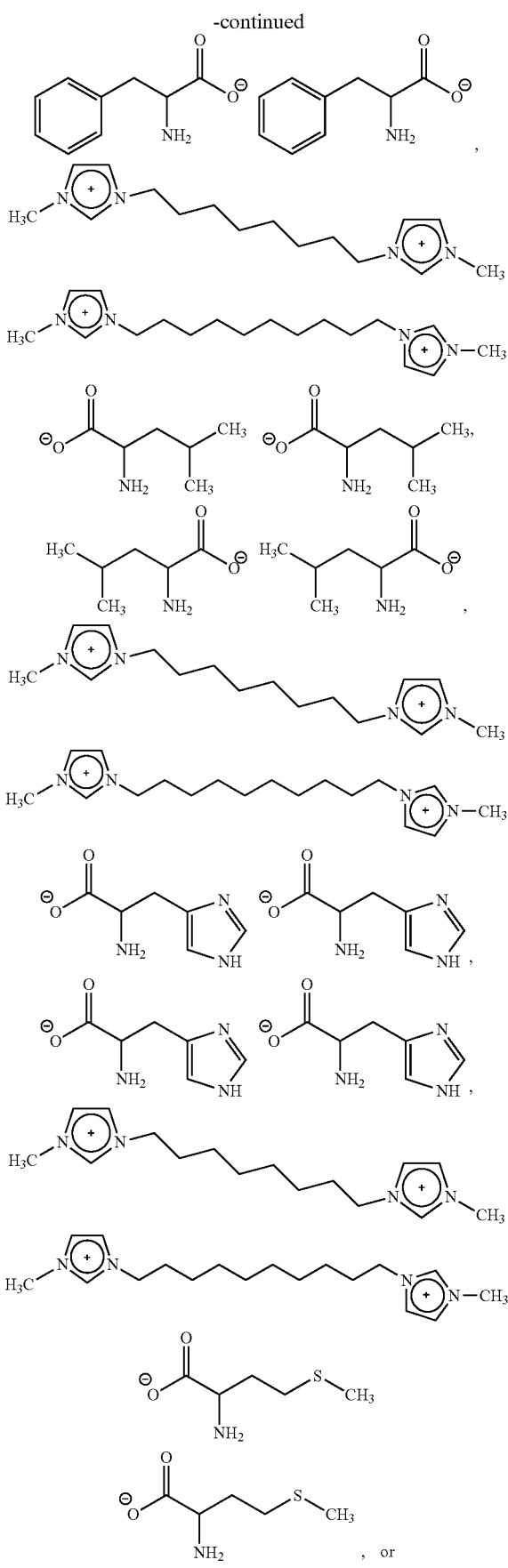

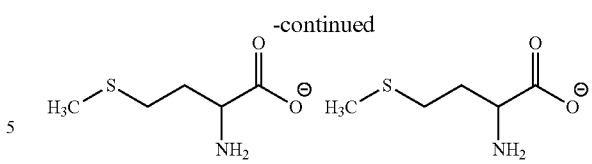

In another aspect, the present disclosure provides a pharmaceutical composition comprising an ionic liquid of the present disclosure and a pharmaceutically acceptable carrier.

In yet another aspect, the present disclosure provides a method of using an ionic liquid comprising a cation of the formula:

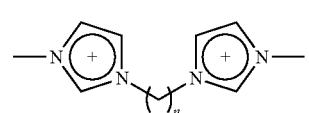

(I)

wherein: n is 2-16; or a cation of the formula:

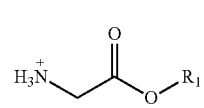

(II)

wherein: $R_1$ is alkyl$_{(C \leq 12)}$, cycloalkyl$_{(C \leq 12)}$, alkenyl$_{(C \leq 12)}$, cycloalkenyl$_{(C \leq 12)}$, alkynyl$_{(C \leq 12)}$, aryl$_{(C \leq 12)}$, aralkyl$_{(C \leq 12)}$, or a substituted version of any one of these groups; and an anion selected from: a β-lactam compound, an amino acid$_{(C \leq 18)}$; phosphate, alkylphosphate$_{(C \leq 12)}$, substituted alkylphosphate$_{(C \leq 12)}$, dialkylphosphate$_{(C \leq 12)}$, substituted dialkylphosphate$_{(C \leq 12)}$, a sugar, ascorbic acid, B(Y$_1$)(Y$_2$)(Y$_3$)(Y$_4$)$^-$, wherein Y$_1$, Y$_2$, Y$_3$, and Y$_4$ are each independently selected from halogen; hydroxyl; amino; alkyl$_{(C \leq 6)}$; alkenyl$_{(C \leq 6)}$; alkynyl$_{(C \leq 6)}$; aryl$_{(C \leq 12)}$; aralkyl$_{(C \leq 12)}$; acyl$_{(C \leq 6)}$; alkoxy$_{(C \leq 6)}$; aryloxy$_{(C \leq 12)}$; acyloxy$_{(C \leq 6)}$; or a substituted version of any of the last nine groups, halide, and N(A$_1$)(A$_2$)$^-$ wherein: A$_1$ and A$_2$ are each independently selected from alkyl$_{(C \leq 12)}$, substituted alkyl$_{(C \leq 12)}$, cycloalkyl$_{(C \leq 12)}$, substituted cycloalkyl$_{(C \leq 12)}$, alkylsulfonyl$_{(C \leq 12)}$, substituted alkylsulfonyl$_{(C \leq 12)}$, cycloalkylsulfonyl$_{(C \leq 12)}$, or substituted cycloalkylsulfonyl$_{(C \leq 12)}$; wherein the method comprises contacting the ionic liquid with one or more surfaces or a part of any surface of a device under conditions suitable to deposit the ionic liquid on the surface thereof. In some embodiments, the ionic liquid does not comprise an ionic liquid wherein when the cation has formula I then the anion is not tetravalent boron compound$_{(C \leq 18)}$, substituted tetravalent boron compound$_{(C \leq 18)}$, halogen, and N(A$_1$)(A$_2$)$^-$ wherein: A$_1$ and A$_2$ are each independently selected from alkyl$_{(C \leq 12)}$, substituted alkyl$_{(C \leq 12)}$, alkylsulfonyl$_{(C \leq 12)}$, or substituted alkylsulfonyl$_{(C \leq 12)}$. In some embodiments, the cation is of formula I. In some embodiments, n is 4, 5, 6, 7, 8, 9, 10, 11, 12, 13, or 14. In some embodiments, n is 6, 7, 8, 9, 10, 11, or 12. In some embodiments, n is 8 or 10. In some embodiments, the cation is further defined by the formula:

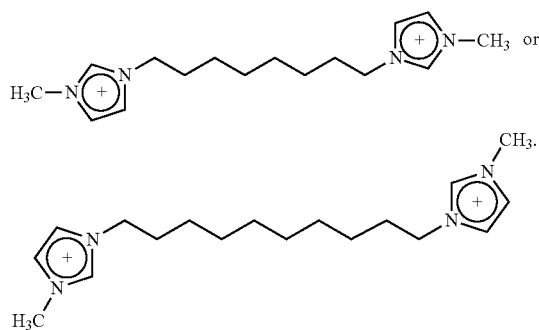

In some embodiments, the cation is of formula II. In some embodiments, $R_1$ is alkyl$_{(C≤12)}$ or substituted alkyl$_{(C≤12)}$. In some embodiments, $R_1$ is alkyl$_{(C≤8)}$ or substituted alkyl$_{(C≤8)}$. In some embodiments, $R_1$ is alkyl$_{(C≤8)}$. In some embodiments, $R_1$ is methyl. In some embodiments, the cation is further defined by the formula:

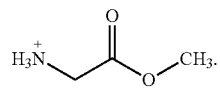

In some embodiments, the anion is an amino acid$_{(C≤12)}$. In some embodiments, the amino acid is an α-amino acid$_{(C≤12)}$. In some embodiments, the α-amino acid$_{(C≤12)}$ is selected from the 20 canonical amino acid. In some embodiments, the amino acid$_{(C≤12)}$ is selected from:

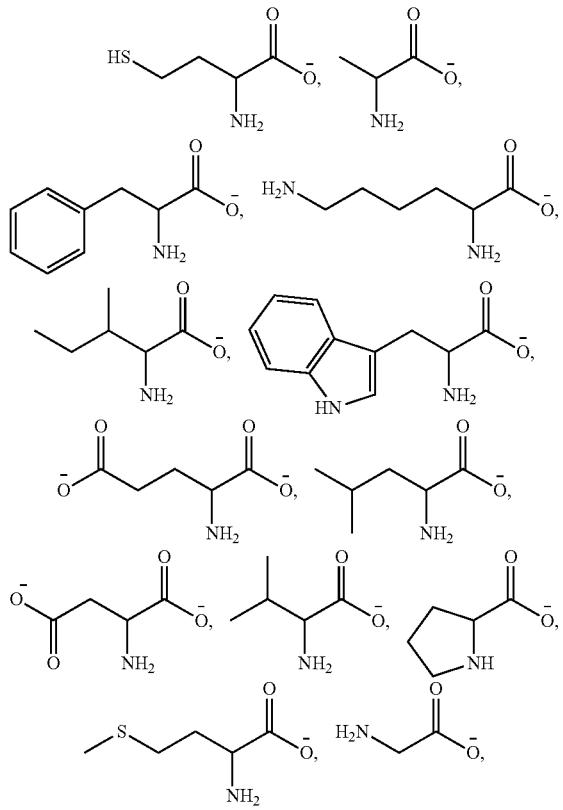

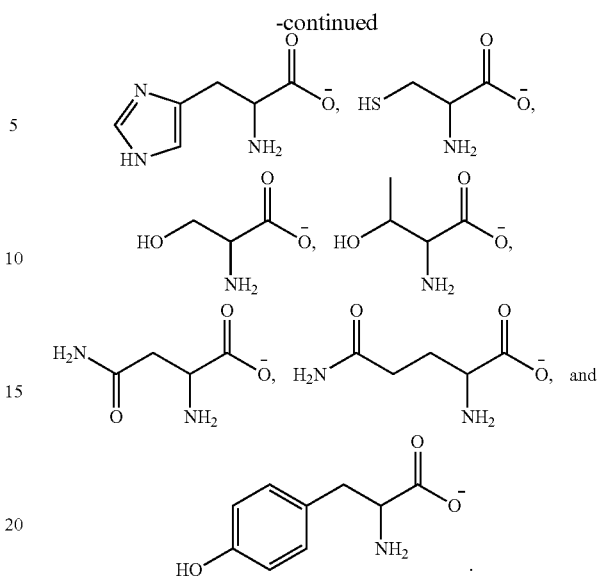

In other embodiments, the anion is phosphate. In other embodiments, the anion is $B(Y_1)(Y_2)(Y_3)(Y_4)^−$, wherein $Y_1$, $Y_2$, $Y_3$, and $Y_4$ are each independently selected from halogen, hydroxyl, amino, alkyl$_{(C≤6)}$, alkenyl$_{(C≤6)}$, alkynyl$_{(C≤6)}$, aryl$_{(C≤12)}$, aralkyl$_{(C≤12)}$, acyl$_{(C≤6)}$, alkoxy$_{(C≤6)}$, aryloxy$_{(C≤12)}$, acyloxy$_{(C≤6)}$, or a substituted version of any of these groups. In some embodiments, $Y_1$ is halogen. In some embodiments, $Y_2$ is halogen. In some embodiments, $Y_3$ is halogen. In some embodiments, $Y_4$ is halogen. In some embodiments, $Y_1$, $Y_2$, $Y_3$, or $Y_4$ is fluoride. In some embodiments, $Y_1$, $Y_2$, $Y_3$, and $Y_4$ are fluoride. In some embodiments, $B(Y_1)(Y_2)(Y_3)(Y_4)^−$ is $BF_4$. In other embodiments, the anion is a sugar. In some embodiments, the anion is ascorbic acid. In some embodiments, the anion is a halogen. In some embodiments, the halogen is bromide. In other embodiments, the anion is ascorbic acid. In other embodiments, the anion is $N(A_1)(A_2)^−$. In some embodiments, $A_1$ is alkylsulfonyl$_{(C≤12)}$ or substituted alkylsulfonyl$_{(C≤12)}$. In some embodiments, $A_1$ is substituted alkylsulfonyl$_{(C≤12)}$. In some embodiments, $A_1$ is substituted alkylsulfonyl$_{(C≤8)}$. In some embodiments, $A_1$ is substituted alkylsulfonyl$_{(C≤6)}$. In some embodiments, the substituted alkylsulfonyl$_{(C≤6)}$ is haloalkylsulfonyl$_{(C≤6)}$. In some embodiments, the haloalkylsulfonyl$_{(C≤6)}$ is fluoroalkylsulfonyl$_{(C≤6)}$. In some embodiments, $A_1$ is trifluoromethylsulfonyl or pentafluoroethylsulfonyl. In some embodiments, $A_2$ is alkylsulfonyl$_{(C≤12)}$ or substituted alkylsulfonyl$_{(C≤12)}$. In some embodiments, $A_2$ is substituted alkylsulfonyl$_{(C≤12)}$. In some embodiments, $A_2$ is substituted alkylsulfonyl$_{(C≤8)}$. In some embodiments, $A_2$ is substituted alkylsulfonyl$_{(C≤6)}$ In some embodiments, the substituted alkylsulfonyl$_{(C≤6)}$ is haloalkylsulfonyl$_{(C≤6)}$. In some embodiments, the haloalkylsulfonyl$_{(C≤6)}$ is fluoroalkylsulfonyl$_{(C≤6)}$. In some embodiments, $A_2$ is trifluoromethylsulfonyl or pentafluoroethylsulfonyl. In some embodiments, the anion is di(trifluoromethylsulfonyl)amide or di(pentafluoroethylsulfonyl)amide. In other embodiments, the anion is a β-lactam compound. In some embodiments, the β-lactam compound is a β-lactam antibiotic. In some embodiments, the β-lactam antibiotic belonging to a class selected from penam, penem, cephem, monobactam, or carbapenem. In some embodiments, the β-lactam antibiotic class belongs to the penam class or the cephem class. In some embodiments, the β-lactam antibiotic further comprises a carboxylate group. In some embodiments, the β-lactam compound is amoxicillin or cefuroxime. In some embodiments, the antibiotic has the formula:

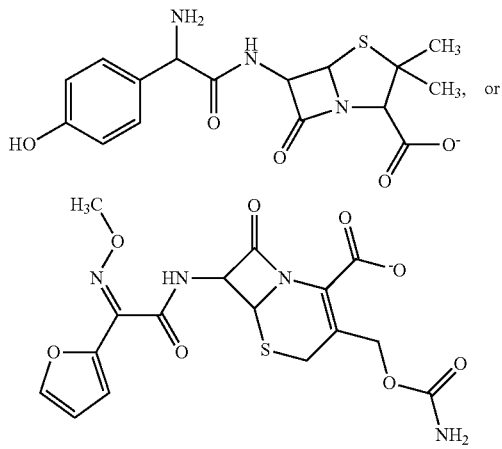

or a pharmaceutically acceptable salt thereof. In some embodiments, the device is a surgical instrument or a trauma, cardiovascular, orthopedic, or dental implant. In some embodiments, the device is an orthopedic implant. In other embodiments, the device is a dental implant. In some embodiments, the device is constructed from titanium, titanium alloy, cobalt, Co—Cr alloy, steel, stainless steel, polyethylene, alumina, or zirconia. In some embodiments, the device is constructed from titanium. In some embodiments, the ionic liquid acts a lubricant on the ionic liquid coated device. In some embodiments, the ionic liquid coated device promotes the adhesion and differentiation of bone and soft tissue forming cells. In some embodiments, the ionic liquid coated device inhibits the growth of a microbe. In some embodiments, the ionic liquid coated device inhibits the adhesion of a biofilm to the device. In some embodiments, the ionic liquid coated device inhibits the growth and adhesion of the microbe or biofilm to the device. In some embodiments, the microbe is a bacteria. In some embodiments, the bacteria is a gram positive bacteria or a gram negative bacteria. In some embodiments, the bacteria is a gram positive bacteria. In some embodiments, the bacteria is a gram negative bacteria. In some embodiments, the device is coated on one surface with the ionic liquid. In some embodiments, the device is coated on all surfaces with the ionic liquid. In some embodiments, the device is coated with a layer of the ionic liquid from about 1 nm to about 5,000 nm. In some embodiments, the layer of the ionic liquid is from about 50 nm to about 2,000 nm. In some embodiments, the layer of the ionic liquid is from about 50 nm to about 800 nm. In some embodiments, the layer of the ionic liquid is from about 100 nm to about 600 nm. In some embodiments, the layer of the ionic liquid is from about 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 850, 900, 950, 1,000, 1,100, 1,200, 1,300, 1,400, 1,500, 1,600, 1,700, 1,800, 1,900, or 2,000 nm, or any range derivable therein.

In another aspect, the present disclosure provides a device wherein the device comprises contacting the device with an ionic liquid

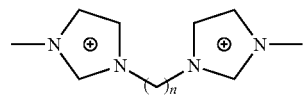

wherein: n is 2-16; or a cation of the formula:

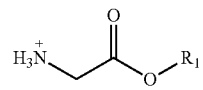

wherein: $R_1$ is $alkyl_{(C \leq 12)}$, $cycloalkyl_{(C \leq 12)}$, $alkenyl_{(C \leq 12)}$, $cycloalkenyl_{(C \leq 12)}$, $alkynyl_{(C \leq 12)}$, $aryl_{(C \leq 12)}$, $aralkyl_{(C \leq 12)}$, or a substituted version of any one of these groups; and an anion selected from: a β-lactam compound, an amino $acid_{(C \leq 18)}$; phosphate, $alkylphosphate_{(C \leq 12)}$, substituted $alkylphosphate_{(C \leq 12)}$, $dialkylphosphate_{(C \leq 12)}$, substituted $dialkylphosphate_{(C \leq 12)}$, a sugar, ascorbic acid, $B(Y_1)(Y_2)(Y_3)(Y_4)^-$, wherein $Y_1$, $Y_2$, $Y_3$, and $Y_4$ are each independently selected from halogen; hydroxyl; amino; $alkyl_{(C \leq 6)}$; $alkenyl_{(C \leq 6)}$; $alkynyl_{(C \leq 6)}$; $aryl_{(C \leq 12)}$; $aralkyl_{(C \leq 12)}$; $acyl_{(C \leq 6)}$; $alkoxy_{(C \leq 6)}$; $aryloxy_{(C \leq 12)}$; $acyloxy_{(C \leq 6)}$; or a substituted version of any of the last nine groups, halide, and $N(A_1)(A_2)^-$ wherein: $A_1$ and $A_2$ are each independently selected from $alkyl_{(C \leq 12)}$, substituted $alkyl_{(C \leq 12)}$, $cycloalkyl_{(C \leq 12)}$, substituted $cycloalkyl_{(C \leq 12)}$, $alkylsulfonyl_{(C \leq 12)}$, substituted $alkylsulfonyl_{(C \leq 12)}$, $cycloalkylsulfonyl_{(C \leq 12)}$, or substituted $cycloalkylsulfonyl_{(C \leq 12)}$; under conditions suitable to deposit the ionic liquid on the device thereof. In some embodiments, the ionic liquid does not comprise an ionic liquid wherein when the cation has formula I then the anion is not $B(Y_1)(Y_2)(Y_3)(Y_4)^-$, wherein $Y_1$, $Y_2$, $Y_3$, and $Y_4$ are each independently selected from halogen; hydroxyl; amino; $alkyl_{(C \leq 6)}$; $alkenyl_{(C \leq 6)}$; $alkynyl_{(C \leq 6)}$; $aryl_{(C \leq 12)}$; $aralkyl_{(C \leq 12)}$; $acyl_{(C \leq 6)}$; $alkoxy_{(C \leq 6)}$; $aryloxy_{(C \leq 12)}$; $acyloxy_{(C \leq 6)}$; or a substituted version of any of the last nine groups, halogen, and $N(A_1)(A_2)^-$ wherein: $A_1$ and $A_2$ are each independently selected from $alkyl_{(C \leq 12)}$, substituted $alkyl_{(C \leq 12)}$, $alkylsulfonyl_{(C \leq 12)}$, or substituted $alkylsulfonyl_{(C \leq 12)}$. In some embodiments, the device is a medical device. In other embodiments, the medical device is a surgical instrument. In other embodiments, the device is an implantable device. In some embodiments, the implantable device is a cardiovascular, trauma, orthopedic implant or dental implant. In some embodiments, the implantable device is a dental implant. In some embodiments, the ionic liquid is deposited on one or more surfaces or any portion of a surface thereof. In some embodiments, the body of the device is constructed from titanium, titanium alloy, cobalt, Co—Cr alloy, steel, stainless steel, polyethylene, alumina, or zirconia.

It is contemplated that any method or composition described herein can be implemented with respect to any other method or composition described herein.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a method, composition, kit, or system that "comprises," "has," "contains," or "includes" one or more recited steps or elements possesses those recited steps or elements, but is not limited to possessing only those steps or elements; it may possess (i.e., cover) elements or steps that are not recited. Likewise, an element of a method, composition, kit, or system that "comprises," "has," "contains," or "includes" one or more recited features possesses those features, but is not limited to possessing only those features; it may possess features that are not recited.

Any embodiment of any of the present methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2B shows that Ti 2p was constant regardless the area analyzed on IL9-coated Ti, demonstrating homogeneous coating profile. Ti 2p BE had different shifts in distinct areas on the surface of IL12-coated Ti revealing heterogeneous coating profile. These findings were further evidenced with AFM images. FIGS. 2D & 2F show the surface morphology of control, IL9-coated Ti and IL12-coated Ti, respectively. It is possible to observe in IL9, which is more hydrophobic, covered the entire surface of Ti while IL12 formed aggregates.

(FIG. 4D) Friction Coefficient of Ti Control, IL9-coated Ti and IL12-coated Ti. (FIG. 4E) Cyclic polarization results for Ti Control, IL9-coated Ti and IL12-coated Ti. Tribology tests were performed using Pin-on-disk set-up. Control Ti (cpTi) as well as disks coated with IL9 and IL2 slid against a Ti6A14V ball under 10N, at 2 Hz during 2000 cycles to simulate oral conditions (Mathew et al., 2012). The adhesion force on coated surfaces was also dependent on IL hydrophobicity. For the IL9-coated Ti surfaces coating adhesion strength values were around 73.5 nN, while IL12-coated Ti showed lower adhesion strength (46.2 nN). These results demonstrate that besides increased coating performance, the more hydrophobic IL9 interacted more strongly with the Ti surface. The results also showed that IL9 was also able to lubricate the surface and reduce the friction coefficient to 0.1, while IL12 did not provide much lubrication. These data demonstrate that the lubricant characteristics may be controlled by the IL formation and degree of hydrophobicity.

FIGS. 5A-D show the cell viability using MC3T3-E1 pre-osteoblasts for. (FIG. 5A) IL-1 (FIG. 5B) IL-13 (FIG. 5C) IL-14 and (FIG. 5D) IL-4.

FIGS. 6C and 6F shows that the cell differentiation and ALP activity is markedly different when treated with the ionic liquid. The ALP activity was measured on both time points and it was observed that both coated and control samples allowed for cell differentiation without statistically significant differences (p<0.05) (FIG. 6F). Cell differentiation was observed after 7 days on Ti control and IL9 coated Ti in which osteoblast are distinguished from stem cells by the purple color of the stain as indicated by the black arrows. Based upon these data, the ionic liquids provided herein continue to allow for cell differentiation and adhesion to a surface. As such, these compounds can be considered to be non-toxic to cells while still maintaining anti-microbial properties.

Figure 1:
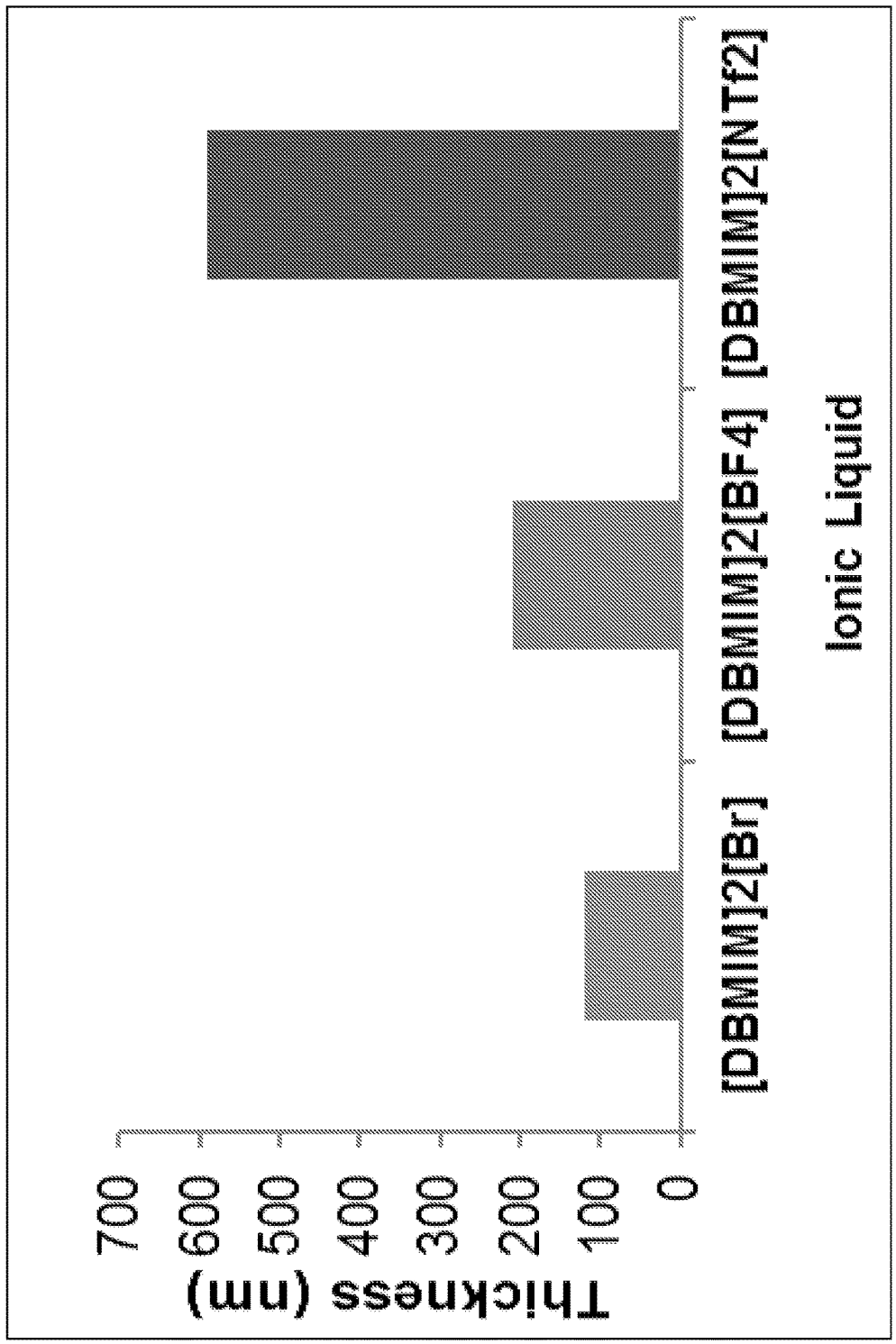
FIG. 1 shows the thickness of film formed by [DBMIM]$_2$[Br], [DBMIM]$_2$[BF$_4$] and [DBMIM]$_2$[NTf$_2$].

Thus, even when the ionic liquid has been coated on a titanium surface, the ionic liquid maintains its antimicrobial activity.

DESCRIPTION OF ILLUSTRATIVE EMBODIMENTS

In some aspects, the present disclosure provides dicationic imidazolium based ionic liquids which may be coated onto a metal or alloy surface of a medical device. In some embodiments, the thin layer of ionic liquid provides lubricating properties to the medical device which can help to prevent wear and corrosion of the metal surface. Additionally, in some embodiments, the ionic liquids provide host cell integrative and/or antimicrobial properties to the device to which they have been deposited. In some embodiments, the present disclosure also provides devices which have been treated with these new ionic liquids and exhibit one or more additional properties such as, but not limited to, acting as lubricants, cell integrative, and as antimicrobial agents.

A. Chemical Definitions

When used in the context of a chemical group: "hydrogen" means —H; "hydroxy" means —OH; "carboxy" means —C(=O)OH (also written as —COOH or —CO$_2$H); "halo" means independently —F, —Cl, —Br or —I; "amino" means —NH$_2$; "nitro" means —NO$_2$; "cyano" means —CN; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⸺" represents a single bond or a double bond. Thus, for example, the formula

includes

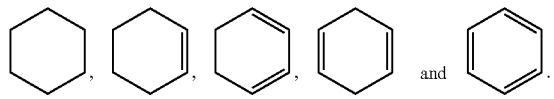

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "⁓", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◂■" means a single bond where the group attached to the thick end of the wedge is "out of the page." The symbol "⬛⬛⬛" means a single bond where the group attached to the thick end of the wedge is "into the page". The symbol "⁓" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

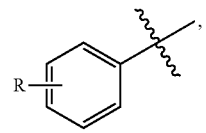

then R may replace any hydrogen atom attached to any of the ring atoms, including a depicted, implied, or expressly defined hydrogen, so long as a stable structure is formed.

When a group "R" is depicted as a "floating group" on a fused ring system, as for example in the formula:

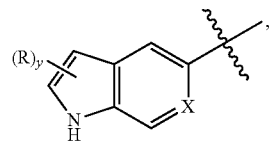

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups, —CH$_2$-(methylene), —CH$_2$CH$_2$—, —CH$_2$C(CH$_3$)$_2$CH$_2$—, and —CH$_2$CH$_2$CH$_2$—, are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, a linear or branched cyclo or cyclic structure, no carbon-carbon double or triple bonds, and no atoms other than carbon and hydrogen. Non-limiting examples of cycloalkyl groups include: —CH(CH$_2$)$_2$ (cyclopropyl), cyclobutyl, cyclopentyl, or cyclohexyl. The term "cycloalkanediyl" when used without the "substituted" modifier refers to a divalent saturated aliphatic group with one or two carbon atom as the point(s) of attachment, a linear or branched cyclo or cyclic structure, no carbon-carbon double or triple bonds, and no atoms other than carbon and hydrogen.

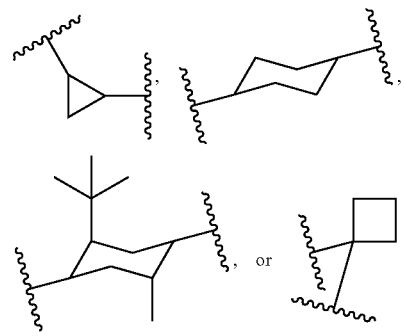

are non-limiting examples of cycloalkanediyl groups. The term "cycloalkylidene" when used without the "substituted" modifier refers to the divalent group =CRR' in which R and R' are taken together to form a cycloalkanediyl group with at least two carbons. Non-limiting examples of alkylidene groups include: =C(CH$_2$)$_2$ and =C(CH$_2$)$_5$. A "cycloalkane" refers to the compound H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted cycloalkyl groups: —C(OH)(CH$_2$)$_2$,

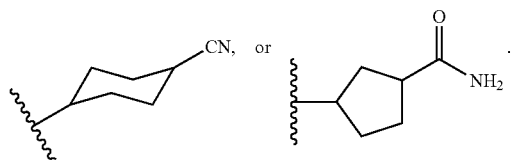 [SMILES: *C1CCC(C#N)CC1 ; *C1CCC(C(N)=O)C1]

The term "alkenyl" when used without the "substituted" modifier refers to a monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH═CH—, —CH═C(CH$_3$)CH$_2$—, —CH═CHCH$_2$—, and

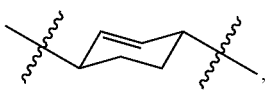

are non-limiting examples of alkenediyl groups. It is noted that while the alkenediyl group is aliphatic, once connected at both ends, this group is not precluded from forming part of an aromatic structure. The terms "alkene" and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH═CHF, —CH═CHCl and —CH═CHBr, are non-limiting examples of substituted alkenyl groups.

The term "cycloalkenyl" when used without the "substituted" modifier refers to a monovalent unsaturated aliphatic group with a carbon atom as the point of attachment, a linear or branched cyclo or cyclic structure, at least one non-aromatic carbon-carbon double bond, no carbon-carbon triple bonds, and no atoms other than carbon and hydrogen. In some non-limiting examples of cycloalkenyl groups include

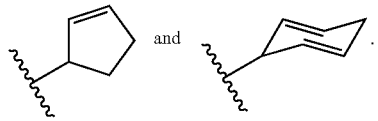 [SMILES: *C1C=CCC1 ; *C1C=CCC=C1]

The term "cycloalkenediyl" when used without the "substituted" modifier refers to a divalent unsaturated aliphatic group with one or two carbon atom(s) as the point(s) of attachment, a linear or branched cyclo or cyclic structure, at least one non-aromatic carbon-carbon double bond, no carbon-carbon triple bonds, and no atoms other than carbon and hydrogen.

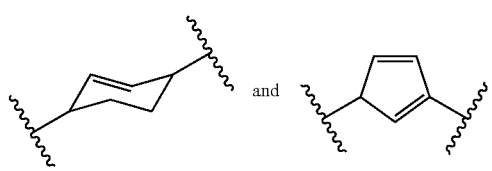 [SMILES: *C1C=CC(*)CC1 ; *C1=CC(*)C=C1]

are non-limiting examples of cycloalkenediyl. It is noted that while the cycloalkenediyl group is aliphatic, once connected at both ends, this group is not precluded from forming part of an aromatic structure. The terms "cycloalkene" and refer to a compound having the formula H—R, wherein R is cycloalkenyl as this term is defined above. The term "olefin" is synonymous with the terms "alkene" or a "cycloalkane" as those terms are defined above. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. In some non-limiting examples of substituted cycloalkenyl include

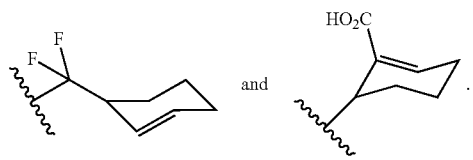 [SMILES: *C(F)(F)C1C=CCCC1 ; *C1CCCC=C1C(=O)O]

The term "alkynyl" when used without the "substituted" modifier refers to a monovalent unsaturated aliphatic group with a carbon atom as the point of attachment, a linear or branched, acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

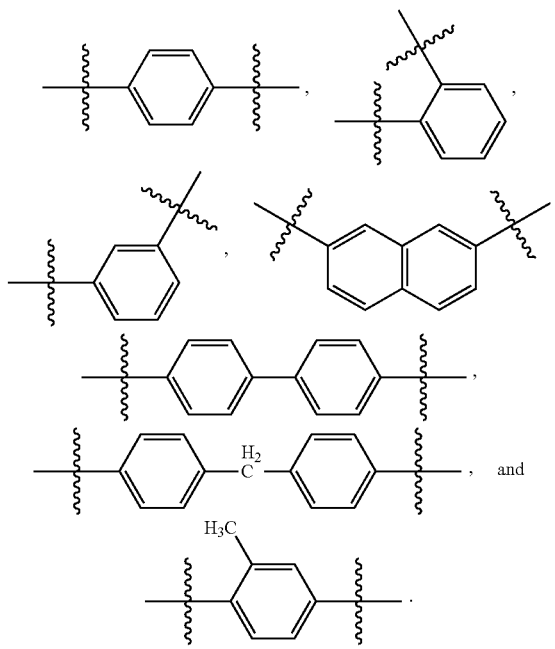

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

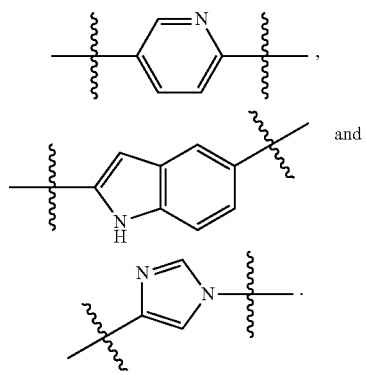

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂.

The term "heteroaralkyl" when used without the "substituted" modifier refers to the monovalent group -alkanediyl-heteroaryl, in which the terms alkanediyl and heteroaryl are each used in a manner consistent with the definitions provided above. Non-limiting examples of heteroaralkyls are: 2-pyridylmethyl and 2-indazolyl-ethyl. When the term heteroaralkyl is used with the "substituted" modifier one or more hydrogen atom from the alkanediyl and/or the heteroaryl group has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —OC(O)CH₃, or —S(O)₂NH₂. Non-limiting examples of substituted heteroaralkyls are: (3-chloroquinolyl)-methyl, and 2-chloro-2-thienyl-eth-1-yl.

The term "acyl" when used without the "substituted" modifier refers to the group —C(O)R, in which R is a hydrogen, alkyl, cycloalkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), and —OC(CH$_3$)$_3$ (tert-butoxy). The terms "cycloalkoxy", "alkenyloxy", "cycloalkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, cycloalkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The terms "alkylthio", "cycloalkylthio", and "acylthio" when used without the "substituted" modifier refers to the group —SR, in which R is an alkyl, cycloalkyl, and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy or cycloalkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can each independently be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "cycloalkylamino", "alkenylamino", "cycloalkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, cycloalkyl, alkenyl, cycloalkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The terms "alkylsulfonyl" and "alkylsulfinyl" when used without the "substituted" modifier refers to the groups —S(O)$_2$R and —S(O)R, respectively, in which R is an alkyl, as that term is defined above. The terms "cycloalkylsulfonyl", "alkenylsulfonyl", "cycloalkenylsulfonyl", "alkynylsulfonyl", "arylsulfonyl", "aralkylsulfonyl", "heteroarylsulfonyl", and "heterocycloalkylsulfonyl" are defined in an analogous manner. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylphosphate" when used without the "substituted" modifier refers to the group —OP(O)(OH)(OR), in which R is an alkyl, as that term is defined above. Non-limiting examples of alkylphosphate groups include: —OP(O)(OH)(OMe) and —OP(O)(OH)(OEt). The term "dialkylphosphate" when used without the "substituted" modifier refers to the group —OP(O)(OR)(OR'), in which R and R' can be the same or different alkyl groups, or R and R' can be taken together to represent an alkanediyl. Non-limiting examples of dialkylphosphate groups include: —OP(O)(OMe)$_2$, —OP(O)(OEt)(OMe) and —OP(O)(OEt)$_2$. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

An "amino acid" is a functional group which contains a —CO$_2$H and a —NH$_2$ group on the same linear carbon skeleton. One or more additional groups can be joined to the methylene linkers between these two groups. In some embodiments, an α-amino acid is an amino acid in which the amino and carboxyl groups are joined by a single methylene bridge, wherein that methylene bridge can have one or two different chemical groups attached. In its preferred embodiment, the term "amino acid" refers to one of the naturally occurring or commercially available amino acids as well as their enantiomers and diastereomers. As used herein, the term "amino acid residue" refers to a divalent amino acid which is linked through both the amine group and carboxylate group, e.g.,

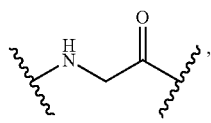 [SMILES: *NCC(*)=O]

which are connected by an alkanediyl$_{(C\leq 6)}$ which has been optionally substituted by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —NHC(O)NH$_2$, —NHC(NH)NH$_2$, or —S(O)$_2$NH$_2$ or an alkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heterocycloalkyl$_{(C\leq 12)}$, acyl$_{(C\leq 12)}$, or a substituted version of any of these groups wherein one or more hydrogen atoms on the chemical group has been substituted with —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —NHC(O)NH$_2$, —NHC(NH)NH$_2$, or —S(O)$_2$NH$_2$. In some embodiments, the amino acid residue is an α-amino acid wherein the alkanediyl is a methylene such that the carbonyl and the amine are joined by a single carbon. In some embodiments, the amino acid is one of the canonical (or naturally occurring) 20 amino acids.

Throughout this application, the term "about" is used to indicate that a value includes the inherent variation of error for the device, the method being employed to determine the value, or the variation that exists among the study subjects.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose, which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half. As used in this application, the terms "IC$_{50}$" and "EC$_{50}$" are used interchangeably.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

B. Ionic Liquids

An ionic liquid (ILs) is a salt which exhibits fluid like properties below 100° C. In some embodiments, the ionic liquid exhibits fluid like properties such as having no definite shape or showing no rigid crystal packing. In some embodiments, non-toxic dicationic ionic liquids with host cell (soft and bone-like cells) activity and antimicrobial properties are envisioned for deposition on the external surfaces of implants. In some aspects, the present disclosure provides ionic liquids with lubricant and antimicrobial activity or only lubricant activity that are envisioned for deposition on modular interfaces of implants. The ionic liquids provided by the present disclosure are shown, for example, above in the summary of the invention section and in the claims below. Some non-limiting examples of ionic liquids that may be used herein include ionic liquids with a cation and an anion wherein the cation of the formula:

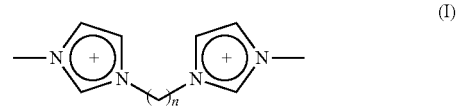
(I)

wherein: n is 2-16; or the cation of the formula:

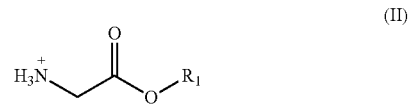
(II)

wherein: $R_1$ is alkyl$_{(C \leq 12)}$, cycloalkyl$_{(C \leq 12)}$, alkenyl$_{(C \leq 12)}$, cycloalkenyl$_{(C \leq 12)}$, alkynyl$_{(C \leq 12)}$, aryl$_{(C \leq 12)}$, aralkyl$_{(C \leq 12)}$, or a substituted version of any one of these groups; and the anion selected from: a β-lactam compound, an amino acid$_{(C \leq 18)}$; phosphate, alkylphosphate$_{(C \leq 12)}$, substituted alkylphosphate$_{(C \leq 12)}$, dialkylphosphate$_{(C \leq 12)}$, substituted dialkylphosphate$_{(C \leq 12)}$, a sugar, ascorbic acid, $B(Y_1)(Y_2)(Y_3)(Y_4)^-$, wherein $Y_1$, $Y_2$, $Y_3$, and $Y_4$ are each independently selected from halogen; hydroxyl; amino; alkyl$_{(C \leq 6)}$; alkenyl$_{(C \leq 6)}$; alkynyl$_{(C \leq 6)}$; aryl$_{(C \leq 12)}$; aralkyl$_{(C \leq 12)}$; acyl$_{(C \leq 6)}$; alkoxy$_{(C \leq 6)}$; aryloxy$_{(C \leq 12)}$; acyloxy$_{(C \leq 6)}$; or a substituted version of any of the last nine groups, halide, and $N(A_1)(A_2)^-$ wherein: $A_1$ and $A_2$ are each independently selected from alkyl$_{(C \leq 12)}$, substituted alkyl$_{(C \leq 12)}$, cycloalkyl$_{(C \leq 12)}$, substituted cycloalkyl$_{(C \leq 12)}$, alkylsulfonyl$_{(C \leq 12)}$, substituted alkylsulfonyl$_{(C \leq 12)}$, cycloalkylsulfonyl$_{(C \leq 12)}$, or substituted cycloalkylsulfonyl$_{(C \leq 12)}$. In some embodiments, the ionic liquid does not comprise an ionic liquid wherein when the cation has formula I then the anion is not tetravalent boron compound$_{(C \leq 18)}$, substituted tetravalent boron compound$_{(C \leq 18)}$, halogen, and $N(A_1)(A_2)^-$ wherein: $A_1$ and $A_2$ are each independently selected from alkyl$_{(C \leq 12)}$, substituted alkyl$_{(C \leq 12)}$, alkylsulfonyl$_{(C \leq 12)}$, or substituted alkylsulfonyl$_{(C \leq 12)}$. Additional non-limiting examples of cations and anions that may be used in ionic liquids of the present disclosure are included below in Tables 1-3.

TABLE 1
Representative ionic liquids with lubricant activity
| Cation | Anion | | |
|---|---|---|---|
| 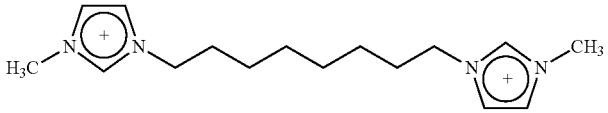 | Br$^\ominus$ | 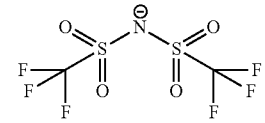 | |
| | 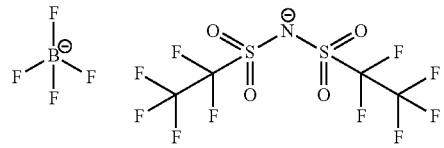 | 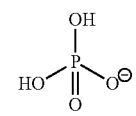 | 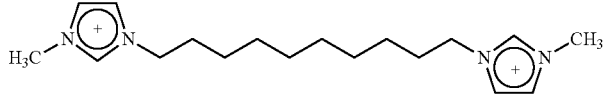 |
| 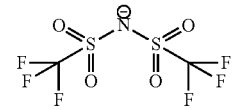 [SMILES: O=S(=O)([N-]S(=O)(=O)C(F)(F)F)C(F)(F)F] | Br$^\ominus$ | 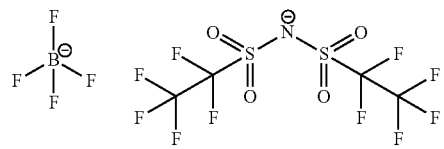 | |
| | 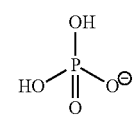 | 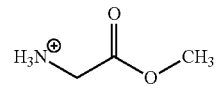 | 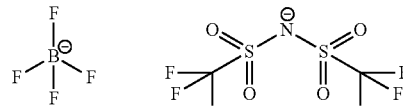 |
| 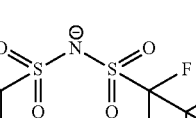 | 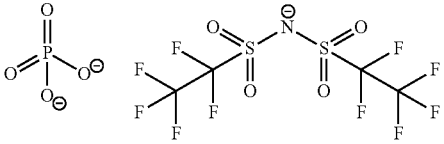 | 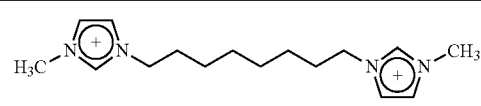 | |
| | 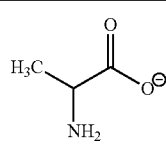 | 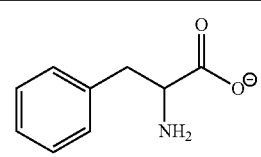 | |
TABLE 2
Representative ionic liquids with osseointegrative activity
| Cation | Anions | |
|---|---|---|
| DBMIM 2 Br | Alanine | Phenyl alanine |

TABLE 2-continued
Representative ionic liquids with osseointegrative activity
| Cation | Anions |
|---|---|
| 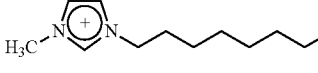 DDMIM 2 Br | 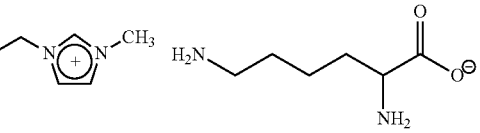 Lysine    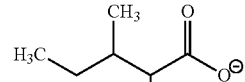 Iso-Leucine |
| | 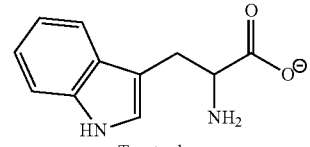 Tryptophan    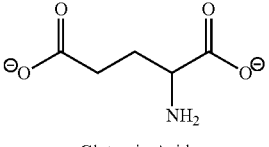 Glutamic Acid |
| | 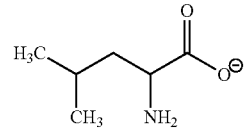 Leucine    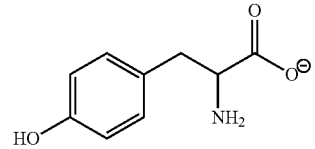 [SMILES: NC(Cc1ccc(O)cc1)C(=O)[O-]] Tyrosine |
| | 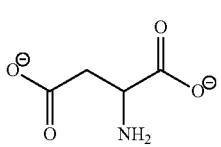 Aspartic Acid    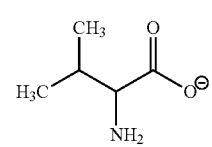 Valine |
| | 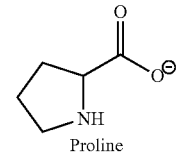 Proline    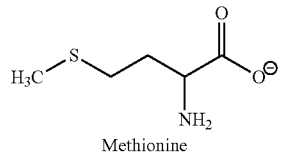 Methionine |
| | 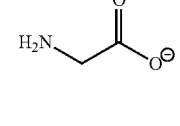 Glycine    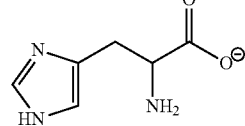 Histidine |
| | 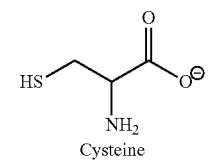 Cysteine    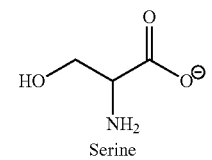 Serine |
| | 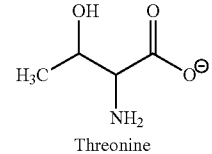 Threonine    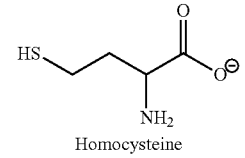 Homocysteine |
| |  Asparagine    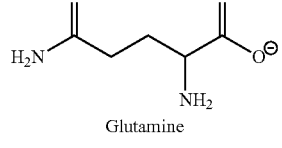 Glutamine |

TABLE 2-continued

Representative ionic liquids with osseointegrative activity

| Cation | Anions |
|---|---|
| |   |
| | Phosphate      Ascorbate |

TABLE 3

Representative ionic liquids with antimicrobial activity

| Cation | Anion |
|---|---|
| 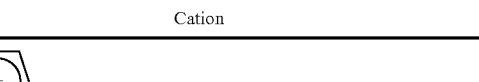 | 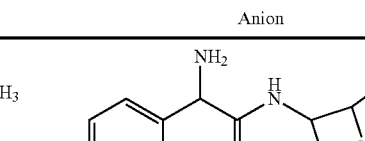 Amoxicilin |
|  Glycin | 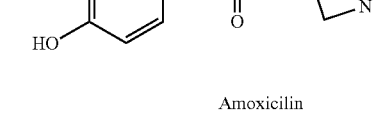 Cefuroxime |

They may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the invention may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in Handbook of Pharmaceutical Salts: Properties, and Use (2002), which is incorporated herein by reference.

Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of the compounds provided herein are within the scope of the invention. It will also be appreciated by those skilled in organic chemistry that many organic compounds can exist in more than one crystalline form. For example, crystalline form may vary from solvate to solvate. Thus, all crystalline forms of the compounds provided herein or the pharmaceutically acceptable solvates thereof are within the scope of the present invention.

C. Properties Of Ionic Liquids

Ionic liquids have a combination of properties that are attractive for applications where two surfaces slide against each other or wherein the surfaces come into contact with an environment filled with an expansive microbiome. Ionic liquids are currently under investigation particularly for applications where conventional oils and other lubricants may not be applicable. Jimenez and Bermudez (2009) reported that reactive alloys such as titanium can be difficult to lubricate, therefore ionic liquids have been attempted as an alternative method to improve lubrication of this material. The formation of ultra-thin ionic liquid films on titanium surfaces ($TiO_2$) may therefore promote improved bio-lubrication. Some studies support the fact that ionic liquids can adhere strongly to metallic substrates forming stable thin-films (Palacio and Bushan, 2008). Moreover, using ionic liquids as a bio-lubricant of modular interfaces can help mitigate fretting-crevice corrosion and surface wear, which can ultimately contribute to better implant performance in vivo. Observations from the literature suggest the use of a few ionic liquid compounds as drug carriers, giving support to their low toxicity for biological applications (Frizzo et al., 2013).

In some aspects, bacterial contamination is a common problem for implants and medical devices which may be solved by the use of ionic liquids. Bacterial contamination can occur shortly after implantation and has been observed to occur on all implant materials regardless of roughness or hydrophobicity (Zhao et al., 2014 and Sánchez et al., 2014). Without wishing to be bound by any theory, it is believed that bacterial adhesion to implants change the electrochemical environment of the implant surface, leading to disruption of this oxide layer (Chin et al., 2007 and Wilson et al., 2015). In a recent in vitro study, the serial passage of dental implants in Streptococcus mutans cultures for 60 days led to significant changes in implant surface morphology, with evidence of corrosion and metal ions generation in solution (Wilson et al., 2015). In a subsequent in vitro study comparing the effects of early and late colonizers on the Ti surface structure, the immersion of implants in S. mutans culture caused significantly more damage to the oxide layer compared to implants immersed in P. gingivalis (Gindri et al., 2014). Thus, the development of the addition of ionic liquids to medical devices and implants may be used to inhibit the growth and development of biofilms and other microbes which reduce the life of the devices. The introduction of longer alkyl chains on the imidazolium cation results in high antimicrobial activity, which consequently lowers the MIC against bacteria (Gindri et al., 2014). The hydrophobicity of both IL cations and anions have been reported to play a role in increasing IL antimicrobial effects. While the anionic portion of the ionic liquid is believed to have a relatively smaller toxic effect. Ionic liquids target the cell membranes of microbes which leads to the ionic liquid's antimicrobial activity. Therefore, a drawback of monocationic ILs and also of other coating technologies is that the effectiveness against bacteria results in toxic effects to host cells. As described herein, introducing a second cationic head reduced IL toxic effects and resulted in a potent strategy to modify the surface of Ti with ILs which maintain their antimicrobial activity. Dicationic ionic liquids provided herein may be used to inhibit the formation of these biofilms and thus lead to a longer life span of the medical device or implant.

In some embodiments, ionic liquid films exhibit a combination of physical, chemical and mechanical properties to meet requirements for in vivo applications as bio-lubricant. In some embodiments, ionic liquids synthesized in this disclosure are designed to exhibit the following desirable properties:

(a) Antimicrobial: In some embodiments, the dicationic ionic liquids provided herein inhibit the formation of bacterial biofilms and replication of microbes and bacteria. Thus, the dicationic ionic liquids provided herein may be used in medical devices or implants to inhibit biofilm formation and prevent the degradation of the medical device or implant in vivo.

(b) Cell Integration: In some embodiments, the dicationic ionic liquid may be used to encourage or promote hard and soft tissue development and host cell (soft and bone-like cells) activity. The dicationic ionic liquids may be used to promote faster healing and development of tissue (both bone and soft tissue) around the implant or medical device, while protecting the medical device or implant surface from damage during healing.

(c) Improved lubrication and corrosion: In some embodiments, ionic liquids or thin-films are selected in such a way to minimize the potential for tribochemical reactions at the contacting interfaces. Additionally, the dicationic ionic liquids may enhance the frictional properties of the medical device or implant or may be used to reduced fretting. Finally, in some embodiments, the use of the ionic liquids provided herein may reduce the damage of the medical device or implant and thus increase the time that the device or implant can be safely used.

The current clinical scenario suggests that techniques providing implant surfaces with activity against bacterial adhesion while also preserving the compatibility of the surface with host cells and protection against corrosion could significantly improve implant integration and function. A variety of surface treatments exist for surface modification of titanium and its alloys. These treatments are divided in two categories: (a) those that produce a diffusion layer and (b) those that produce an overlay layer (Hendry and Pilliar, 2001). A few of these methods have been proposed to enhance wear resistance and host cell integration by altering the nature of the surface. These include ion implantation, nitride (TiN) coating (Goldberg and Gilbert, 2004), amorphous carbon coatings (Hendry and Pilliar, 2001), plasma sprayed hydroxyapatite (Clyne et al., 1998), thermal and anodic oxidation (Kumar et al., 2010). However, most of the typical surface treatments are not applicable to the irregular geometries of modular interfaces of orthopedic or dental implants (abutment-screw interface) because they alter roughness or do not promote the formation of homogeneous layers on the substrate. Rough coatings have been reported to fail releasing fragments in the body. Enhanced release of metal ions can also result, which in conjunction with metal particles and fragments can contribute to a third body mechanism in vivo (Gibson and Stamm, 2002). In summary, little has been reported on the effectiveness of such modification processes on the fretting corrosion behavior of modular implants (Hendry and Pilliar, 2001). Contrary to typical surface treatments on the outer interfaces of implants, which aim to improve host cell integration such as ossseointegration, surface roughness in modular tapers should not be altered. Therefore, in some embodiments, the requirements and performance to qualify ionic liquid films as a bio-lubricant in the disclosure include:

(a) Capability to form thin films with homogenous structures: The ability to form films determines the performance of the boundary lubrication. The polar nature of ionic liquid films may facilitate physical adsorption in the boundary lubrication regime. In some embodiments, film thickness needs to be adequate in such a way to not interfere with the small tolerances of modular interfaces or surgical site.

(b) Improvement in tribological properties of Ti under sliding conditions: Adhesion strength is a useful property if a thin-film is intended to protect a surface and improve lubrication conditions. In this disclosure, in some aspects, the binding strength should not be too weak to the point of breaking in the presence of physiological fluids, or should not be too strong to the point of interfering with the natural micro-movement of the surfaces in contact. In some embodiments, ionic films result in better friction reducing and anti-wear properties under physiologically relevant sliding conditions or insertion against bone.

Without being bound by theory, numerous studies have demonstrated that peptide modified surfaces influence short and long-term cell responses such as improve of osseointegration and other host cell integration. On oxide surfaces such as titanium, researchers have identified carboxylate groups as the preferential peptide binding groups because of their strong electrostatic interactions with the charged surface. In some embodiments, dicationic ionic liquids can be used to improve the host cell integration (osseointegration or gingival epithelium growth for dental implants) of implants in vivo.

D. Medical Devices or Implants

The interfaces of orthopedic and dental implants are designed with non-conforming geometries and tight tolerances to ensure minimum micromotion during loading. These conditions impose several constraints in terms of surface treatments and modification of the surface of contacting interfaces. Therefore, modular areas, for example, the head-neck, neck-stem, and neck-neck counterparts of hip implants, or screw-abutment of dental implants represent regions where achieving improved wear properties via ultra-thin films could contribute for improved performance of these designs. Ionic liquids have been demonstrated to provide improved wear properties of contacting metallic surfaces under harsh boundary conditions and high temperatures. According to previous studies, the decomposition temperatures of imidazolium ionic liquids are generally above 350° C. with glass transition temperatures below −50° C. (Liu et al., 2009). This gives ionic liquids functionality in a broad range of temperatures, combined with the fact that with high polarity these ionic liquids form very strong adsorption films and tribochemical reactions that will contribute to their prominent anti-wear capability (Liu et al., 2009). In some embodiments, surfaces coated with ultra-thin ionic liquids possess a combination of properties such as but not limited to osseointegrative or antimicrobial as well as lubricant properties. In some embodiments, implant surfaces treated with these ultra-thin ionic liquid films fulfill the following requirements:

(a) Ability to coat irregular geometries: In some embodiments, ionic liquids films deposited on the surface of modular implants conform to the geometry of the parts not interfering with tolerances and part assembly.

(b) Treated surfaces should survive physiological conditions: In some embodiments, ultra-thin ionic liquids films survive the mechanical and biological conditions imposed by the physiological environment (stresses, temperature, and pH).

In some aspects, the ionic liquids provided herein may be used to coat or incorporate into a dental implant. Some non-limiting examples of dental implants are described in U.S. Pat. Nos. 6,039,568 and 8,075,312 or U.S. Patent Application Nos. 2005/0037319 or 2012/0077151, which are all incorporated herein by reference.

E. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A. Example 1

Ionic Liquids and Synthesis of Ionic Liquids

1. Synthesis

Ionic liquids were demonstrated in previous studies to be non-volatile, non-flammable, thermo-oxidative stable and highly ionic conductive, which make them green-lubricants. The study of Jimenez and Bermudez (2009), which discussed the viability of using ionic liquids for titanium lubrication under severe contact conditions, gave an important indication of the applicability of ionic liquids for protection of titanium implants.

The ionic liquids provided herein are based on dicationic amphiphiles formed by two imidazolium rings linked by an alkyl chain and an anionic counterpart. The first step is a simple synthetic procedure consisted of alkylation reaction of methylimidazole, nucleophilic substitution reaction according to the scheme presented in Scheme 1. The second step consists in the anion exchange, which generally consists of metathesis reactions. Both inorganic and organic anions can be used to obtain ionic liquids with different characteristics. It has been reported that inorganic anions such as NTf$_2^-$ (Bis(trifluoromethane)sulfonamide) confer good lubricant properties to ILs due its high hydrophobicity and stability (Jimenez et al., 2010). Likewise, the use of organic anions can be a good alternative to improve ionic liquid biocompatibility. The docusate, for example, is a hydrophobic anion that has been used to synthetize ionic liquids with pharmacological activity. The ibuprofenate, which is a pharmaceutical used as anti-inflammatory agent, is also employed in the synthesis of ionic liquids with pharmaceutical activities (Frizzo et al., 2013). In metathesis reaction the cation and anion in their available salt forms are separately dissolved in a solvent (e.g., water, methanol, ethanol, or acetone), and allowed to stir with heating to about 60° C. (if necessary) or at room temperature, as shown in Scheme 2.

Organic anions have also been reported as being a good alternative as bio-lubricants due their good biocompatibility properties. Furthermore, this class of anions provides an important way of introducing complex reactive functionalities and architectures to a metal surface. Some studies have demonstrated amino acid adsorption on TiO$_2$ surface, which showed the preferential interaction of the carboxylate groups with the surface Ti$^{4+}$ cations (Pradier et al., 2012). Therefore, the application of ionic liquids with anionic moieties from amino acids shows great potential to work as bio-lubricant. Fukumoto et al. (2005) synthesized ionic liquids from a series of amino acids using a different method that involved preparing imidazolium hydroxide to neutralize a series of amino acids. In this procedure the 1-Ethyl-3-methylimidazolium hydroxide ([emim][OH]) aqueous solution was prepared from 1-ethyl-3-methylimidazolium bromide using anion exchange resin. The reaction scheme is represented in Scheme 3 (Fukumoto et al., 2005). Both cations and anions used in the later studies (b and c) are summarized in Table 4.

Scheme 1. Alkylation reaction for synthesis of ionic liquids.

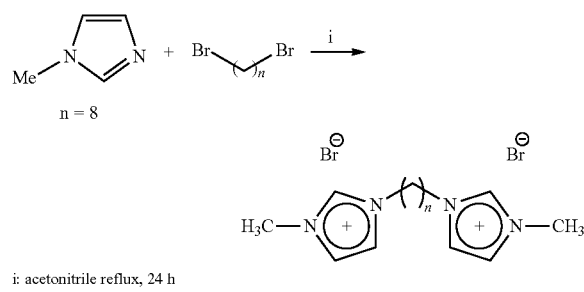

i: acetonitrile reflux, 24 h

Scheme 2. Metathesis reaction for synthesis of ILs.

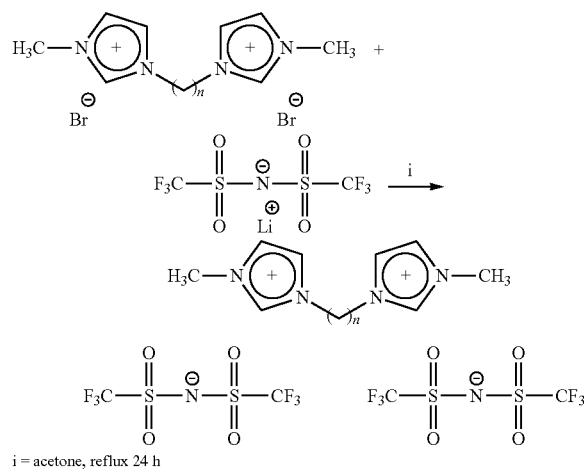

i = acetone, reflux 24 h

Scheme 3. Synthesis of ILs adapted from Fukumoto et al., 2005.

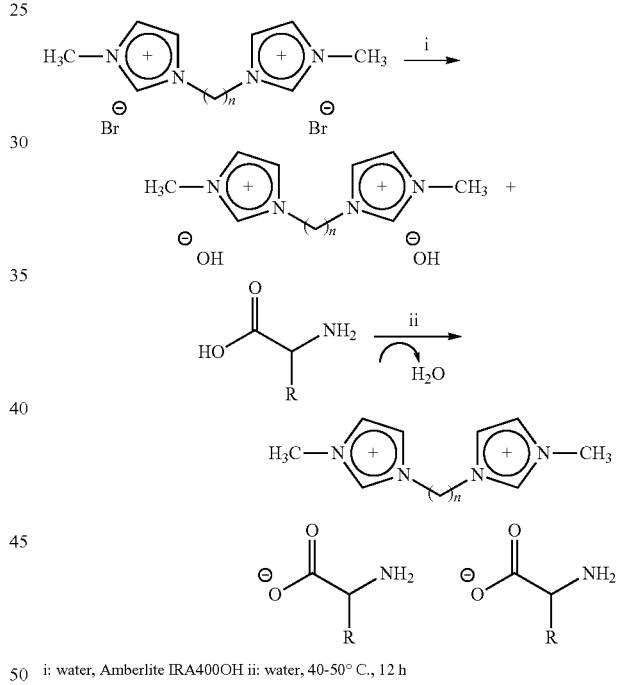

i: water, Amberlite IRA400OH ii: water, 40-50° C., 12 h

2. Ionic Liquids

TABLE 4

Structures of ionic Liquids Used Herein

| Ionic Liquid | Structure |
|---|---|
| IL-1 [DBMIM]$_2$ [Br] | 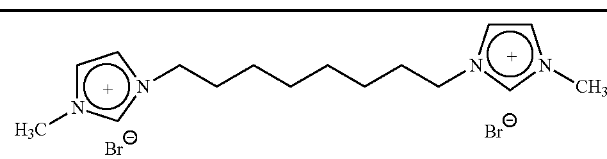 |

TABLE 4-continued
Structures of ionic Liquids Used Herein
| Ionic Liquid | Structure |
|---|---|
| IL-2 | 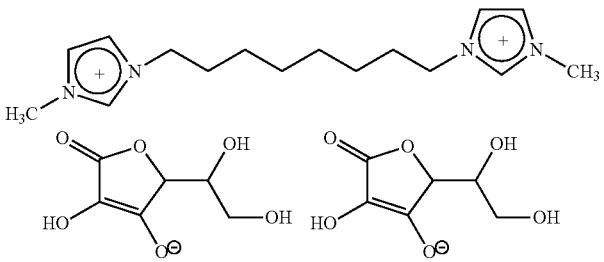 |
| IL-3 | 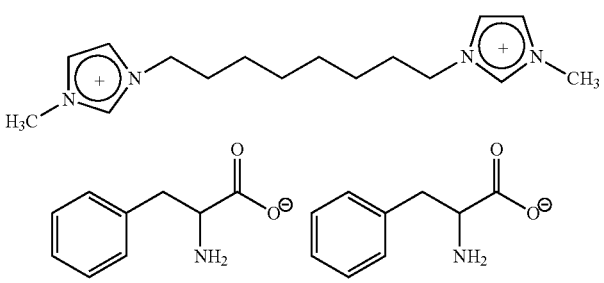 |
| IL-4 | 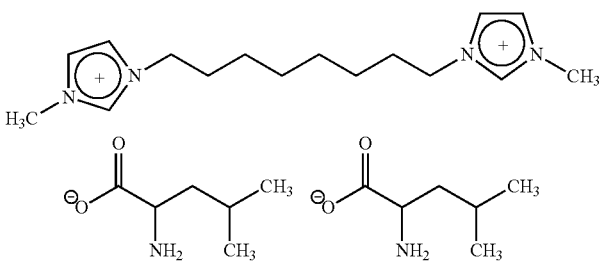 |
| IL-5 | 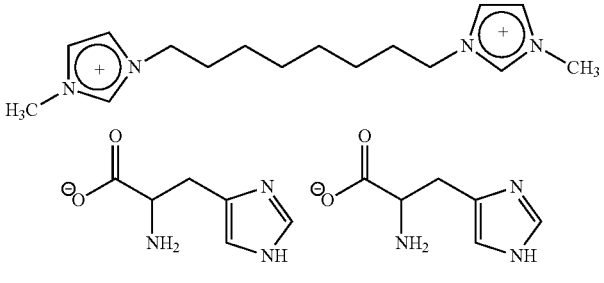 |
| IL-6 | 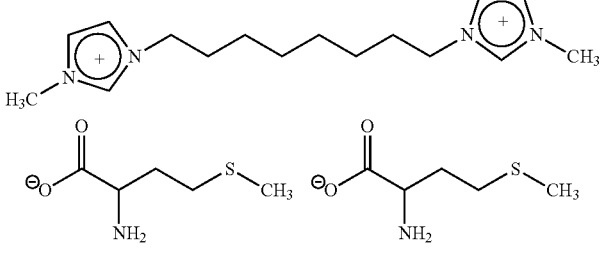 |
| IL-7 | 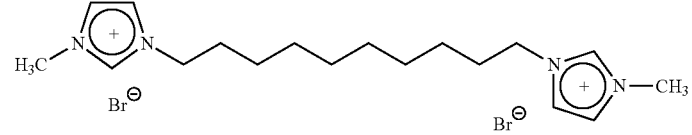 |

TABLE 4-continued
Structures of ionic Liquids Used Herein
| Ionic Liquid | Structure |
|---|---|
| IL-8 | 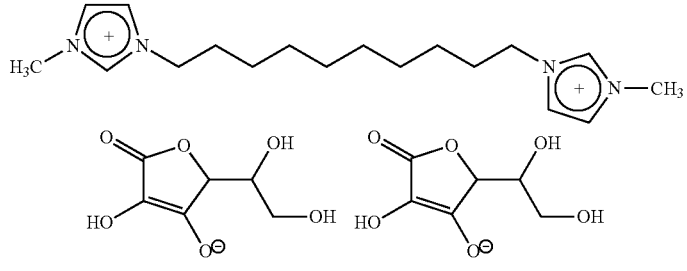 |
| IL-9 | 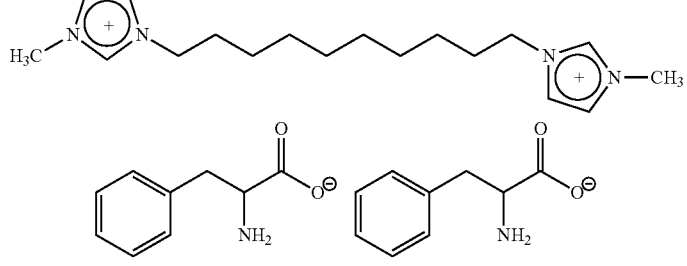 |
| IL-10 | 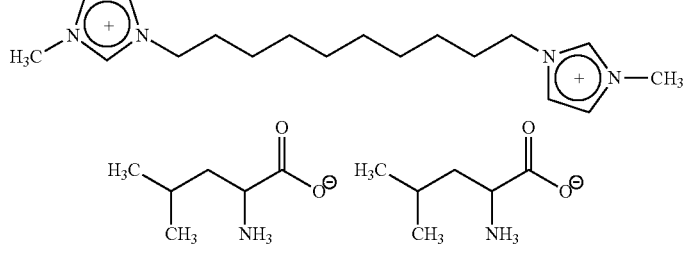 |
| IL-11 | 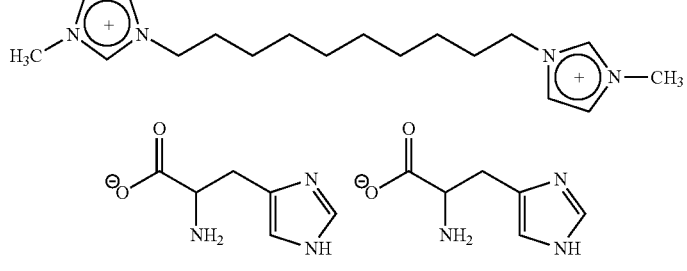 |
| IL-12 | 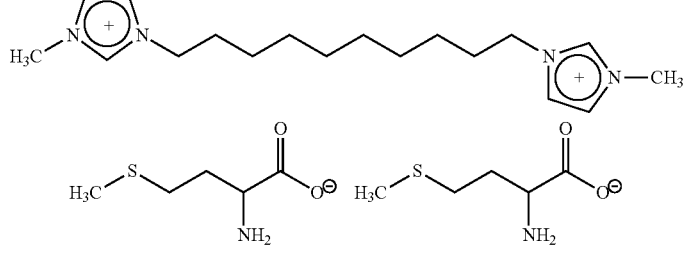 |
| IL-13 | 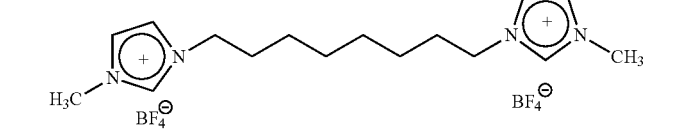 |

TABLE 4-continued

Structures of ionic Liquids Used Herein

| Ionic Liquid | Structure |
|---|---|
| IL-14 | [Structure: 1,8-bis(3-methylimidazolium-1-yl)octane bis(bis(trifluoromethylsulfonyl)imide)] |
| IL-15 | [Structure: 1,9-bis(3-methylimidazolium-1-yl)nonane bis(tetrafluoroborate)] |
| IL-16 | [Structure: 1,10-bis(3-methylimidazolium-1-yl)decane bis(bis(trifluoromethylsulfonyl)imide)] |

2. Spectra Data for Ionic Liquids 1,8-bis(3-methylimidazolium-1-yl) octane bromide (IL-1): $C_{16}H_{28}Br_2N_4$, MW: 436.23 g/mol; $T_g$: −37.91° C.; $^1$H NMR (400 MHz, DMSO): δ 9.28 (s, 2H), 7.82 (s, 2H), 7.74 (s, 2H), 4.18 (t, 4H), 3.87 (s, 6H), 1.78 (qui, 4H), 1.26 (m, 8H). $^{13}$C NMR (100.32 MHz, DMSO): δ 136.4 (2 C), 123.4 (2 C), 122.1 (2 C), 48.6 (2 C), 35.7 (2 C), 29.2 (2 C), 28.0 (2 C), 25.2 (2 C). MS m/z molecular ion (M+): 355.

1,8-Bis(3-methylimidazolium-1-yl)octane diascorbate (IL-2). $C_{28}H_{44}N_4O_{12}$, MW: 628.676 g/mol; from 4.3 g (10 mmol) of IL-1 and 3.5 g (20 mmol) of L-ascorbic acid, 4.4 g of IL-2 was obtained (yield: 71%); $T_g$: 26.65° C.; $^1$H NMR (500 MHz, DMSO-$d_6$): d 9.21 (s, 2H), 7.77 (s, 2H), 7.70 (s, 2H), 4.16 (t, 4H), 4.07 (d, 2H, ascorbate), 3.86 (s, 6H), 3.45 (m, 6H, ascorbate), 1.77 (qui, 4H), 1.27 (m, 8H). $^{13}$C NMR (125 MHz, DMSO-$d_6$): d 172.99 (2C, ascorbate), 136.43 (2C), 123.45 (2C), 122.08 (2C), 113.01 (2C, ascorbate), 79.19 (2C, ascorbate), 71.90 (2C, ascorbate), 63.81 (2C, ascorbate), 48.52 (2C), 35.58 (2C), 29.21 (2C), 28.01 (2C), 25.26 (2C). MS m/z molecular ion: 276.081 (cation), 175.059 (anion).

1,8-Bis(3-methylimidazolium-1-yl)octane diphenylalanine (IL-3). $C_{36}H_{52}N_6O_4$, MW: 632.850 g/mol; from 4.3 g (10 mmol) of IL-1, and 3.3 g (20 mmol) of L-phenylalanine, 5.0 g of IL-3 was obtained (yield: 82%); $T_g$: 25.18° C.; $^1$H NMR (500 MHz, DMSO-$d_6$): d 9.67 (s, 2H), 7.78 (s, 2H), 7.75 (s, 2H), 7.21 (m, 8H, phenylalanine), 7.13 (t, 2H, phenylalanine), 4.16 (t, 4H), 3.86 (s, 6H), 3.07 (d, 2H, phenylalanine), 3.01 (d, 2H, phenylalanine), 2.46 (t, 2H, phenylalanine), 1.76 (qui, 4H), 1.25 (m, 8H). $^{13}$C NMR (125 MHz, DMSO-$d_6$): d 176.48 (2C, phenylalanine), 140.91 (2C, phenylalanine), 136.97 (2C), 128.95 (2C, phenylalanine), 127.51 (4C, phenylalanine), 125.05 (2C, phenylalanine), 123.24 (2C), 121.90 (2C), 57.71 (2C, phenylalanine), 48.32 (2C), 42.11 (2C, phenylalanine), 35.31 (2C), 29.09 (2C), 27.82 (2C), 25.08 (2C). MS m/z molecular ion: 276.081 (cation), 164.210 (anion).

1,8-Bis(3-methylimidazolium-1-yl)octane dileucine (IL-4). $C_{28}H_{52}N_6O_4$, MW: 536.762 g/mol; from 4.3 g (10 mmol) of IL-1, and 2.6 g (20 mmol) of L-leucine, 4.2 g of IL-4 was obtained (yield: 78%); $T_g$: 40.07° C.; $^1$H NMR (500 MHz, DMSO-$d_6$): d 9.73 (s, 2H), 7.82 (s, 2H), 7.74 (s, 2H), 4.18 (t, 4H), 3.87 (s, 6H), 2.79 (t, 2H, leucine), 1.77 (qui, 4H), 1.70 (t, 2H, leucine), 1.41 (t, 2H, leucine), 1.27 (m, 8H), 1.06 (m, 2H, leucine), 0.85 (d, 6H, leucine), 0.81 (d, 6H, leucine). $^{13}$C NMR (125 MHz, DMSO-$d_6$): d 177.61 (2C, leucine), 137.26 (2C), 123.44 (2C), 122.12 (2C), 54.46 (2C, leucine), 48.51 (2C), 45.61 (2C, leucine), 35.53 (2C), 29.28 (2C), 28.04 (2C), 25.29 (2C), 24.58 (2C, leucine), 23.65 (3C, leucine), 21.83 (3C, leucine). MS m/z molecular ion: 276.081 (cation), 130.367 (anion).

1,8-Bis(3-methylimidazolium-1-yl)octane dihistidine (IL-5). C28H44N10O4, MW: 584.726 g/mol; from 4.3 g (10 mmol) of IL-1, and 3.1 g (20 mmol) of L-histidine, 4.7 g of IL-5 was obtained (yield: 81%); $T_g$: 21.11° C.; $^1$H NMR (500 MHz, DMSO-$d_6$): d 9.54 (s, 2H), 7.80 (s, 2H), 7.73 (s, 2H), 7.42 (s, 2H, histidine), 6.64 (s, 2H, histidine), 4.16 (t, 4H), 3.87 (s, 6H), 3.06 (d, 2H, histi-dine), 2.88 (d, 2H, histidine), 2.45 (d, 2H, histidine), 1.77 (qui, 4H), 1.23 (m, 12H). $^{13}$C NMR (500 MHz, DMSO-$d_6$): d 176.36 (2C, histidine), 136.83 (2), 133.80 (2C, histidine), 123.30 (2C), 121.97 (2C), 56.14 (2C, histidine), 48.40 (2C), 35.41 (2C), 33.51 (2C, histidine), 29.09 (2C), 27.86 (2C), 25.12 (2C). MS m/z molecular ion: 276.081 (cation), 154.287 (anion).

1,8-Bis(3-methylimidazolium-1-yl)octane dimethionine (IL-6). $C_{26}H_{48}N_{10}O_4$, MW: 600.882 g/mol; from 4.6 g (10 mmol) of IL-1, and 3.0 g (20 mmol) of L-methionine, 4.3 g of IL-6 was obtained (yield: 75%); $T_g$: 47.41° C.; $^1$H NMR (500 MHz, DMSO-$d_6$): d 9.66 (s, 2H), 7.82 (s, 2H), 7.75 (s, 2H), 4.16 (t, 4H), 3.88 (s, 6H), 2.92 (d, 2H, methionine), 2.48 (m, 4H, methionine), 2.00 (s, 6H, methionine), 1.78 (m, 4H), 1.78 (t, 2H, methionine), 1.51 (t, 2H), 1.27 (m, 12H). $^{13}$C NMR (125 MHz, DMSO-$d_6$): d 176.56 (2C, methionine), 137.19 (2C), 123.34 (2C), 122.05 (2C), 55.29 (2C, methionine), 48.39 (2C), 35.86 (2C, methionine), 35.42 (2C), 30.78 (2C, methionine), 29.18 (2C), 2.92 (2C), 25.18 (2C), 14.54 (2C, methionine). MS m/z molecular ion: 276.081 (cation), 148.271 (anion).

1,10-Bis(3-methylimidazolium-1-yl)decane dibromide (IL-7). $C_{18}H_{32}Br_2N_4$, MW: 464.28 g/mol; from 8.2 g (50 mmol) of 1H-methylimidazole, and 15.0 g (100 mmol) of 1,10-dibromodecane, 22.3 g of IL-7 was obtained (yield: 96%); MP: 130.77° C. or $T_g$: 21.21° C.; $^1$H NMR (500 MHz, DMSO-$d_6$): d 9.26 (s, 2H), 7.83 (s, 2H), 7.75 (s, 2H), 4.18 (t, 4H), 3.88 (s, 6H), 1.78 (m, 4H), 1.25 (m, 12H). $^{13}$C NMR (125 MHz, DMSO-$d_6$): d 136.3 (2CH), 123.4 (2CH), 122.1 (2CH), 48.7 (2CH2), 35.6 (2CH3), 29.2 (2CH2), 28.5 (2CH2), 28.1 (2CH2), 25.3 (2CH2). MS m/z molecular ion: 304.262 (cation), 79.350 (anion).

1,10-Bis(3-methylimidazolium-1-yl)decane diascorbate (IL-8). $C_{28}H_{44}N_4O_{12}$, MW: 654.714 g/mol; from 4.6 g (10 mmol) of IL-7, and 3.5 g (20 mmol) of L-ascorbic acid, 4.9 g of IL-8 was obtained (yield: 75%); $T_g$: 60.13° C.; $^1$H NMR (500 MHz, DMSO-$d_6$): d 9.14 (s, 2H), 7.76 (s, 2H), 7.69 (s, 2H), 4.22 (d, 2H, ascorbate), 4.14 (t, 4H), 3.86 (s, 6H), 3.43 (m, 6H, ascorbate), 1.77 (qui, 4H), 1.25 (m, 12H). $^{13}$C NMR (125 MHz, DMSO-d6): d 172.45 (2C, ascorbate), 136.47 (2C), 123.55 (2C), 122.18 (2C), 114.48 (2C, ascorbate), 77.70 (2C, ascorbate), 70.76 (2C, ascorbate), 63.23 (2C, ascorbate), 48.72 (2C), 35.58 (2C), 29.35 (2C), 28.70 (2C), 28.32 (2C), 25.46 (2C). MS m/z molecular ion: 304.262 (cation), 175.279 (anion).

1,10-Bis(3-methylimidazolium-1-yl)decane diphenylalanine (IL-9). $C_{36}H_{52}N_6O_4$, MW: 632.850 g/mol; from 4.6 g (10 mmol) of IL-7, and 3.3 g (20 mmol) of L-phenylalanine, 4.7 g of IL-9 was obtained (yield: 74%); $T_g$: 48.25° C.; $^1$H NMR (500 MHz, DMSO-$d_6$): d 9.49 (s, 2H), 7.78 (s, 2H), 7.72 (s, 2H), 7.19 (m, 8H, phenylalanine), 7.12 (t, 2H, phenylalanine), 4.15 (t, 4H), 3.85 (s, 6H), 3.02 (d, 4H, phenylalanine), 2.41 (t, 2H, phenylalanine), 1.76 (qui, 4H), 1.23 (m, 12H). $^{13}$C NMR (125 MHz, DMSO-$d_6$): d 176.32 (2C, phenylalanine), 141.40 (2C, phenylalanine), 137.07 (2C), 129.12 (2C, phenylalanine), 127.68 (4C, phenylalanine), 125.16 (2C, phenylalanine), 123.44 (2C), 122.12 (2C), 57.98 (2C, phenylalanine), 48.57 (2C), 42.58 (2C, phenylalanine), 35.55 (2C), 29.34 (2C), 28.63 (2C), 28.26 (2C), 25.41 (2C). MS m/z molecular ion: 304.262 (cation), 164.184 (anion).

1,10-Bis(3-methylimidazolium-1-yl)decane dileucine (IL-10). $C_{30}H_{56}N_6O_4$, MW: 564.82 g/mol; from 4.6 g (10 mmol) of IL-7, and 2.6 g (20 mmol) of L-leucine, 4.3 g of IL-10 was obtained (yield: 78%); $T_g$: 33.92° C.; $^1$H NMR (500 MHz, DMSO-$d_6$): d 9.87 (s, 2H), 7.84 (s, 2H), 7.77 (s, 2H), 4.18 (t, 4H), 3.88 (s, 6H), 2.78 (t, 2H, leucine), 1.77 (qui, 4H), 1.70 (t, 2H, leucine), 1.41 (t, 2H, leucine), 1.24 (m, 12H), 1.05 (m, 2H, leucine), 0.83 (d, 6H, leucine), 0.80 (d, 6H, leucine). $^{13}$C NMR (125 MHz, DMSO-$d_6$): d 179.72 (2C, leucine), 137.32 (2C), 123.25 (2C), 121.96 (2C), 54.39 (2C, leucine), 48.34 (2C), 45.85 (2C, leucine), 35.30 (2C), 29.23 (2C), 28.47 (2C), 28.10 (2C), 25.25 (2C), 24.41 (2C), 23.48 (3C, leucine), 21.63 (3C, leucine). MS m/z molecular ion: 304.262 (cation), 130.367 (anion).

1,10-Bis(3-methylimidazolium-1-yl)decane dihistidine (IL-11). $C_{30}H_{48}N_{10}O_4$, MW: 612.780 g/mol; from 4.6 g (10 mmol) of IL-7, and 3.1 g (20 mmol) of L-histidine, 4.4 g of IL-11 was obtained (yield: 72%); $T_g$: 39.33° C.; $^1$H NMR (500 MHz, DMSO-$d_6$): d 9.55 (s, 2H), 7.81 (s, 2H), 7.73 (s, 2H), 7.42 (s, 2H, histidine), 6.64 (s, 2H, histidine), 4.16 (t, 4H), 3.87 (s, 6H), 3.06 (d, 2H, histidine), 2.88 (d, 2H, histidine), 2.46 (d, 2H, histidine), 1.77 (qui, 4H), 1.23 (m, 12H). $^{13}$C NMR (125 MHz, DMSO-$d_6$): d 177.08 (2C, histidine), 137.02 (2), 134.08 (2C, histidine), 123.46 (2C), 122.14 (2C), 56.53 (2C, histidine), 48.58 (2C), 35.55 (2C), 33.15 (2C, histidine), 29.34 (2C), 28.60 (2C), 28.24 (2C), 25.39 (2C). MS m/z molecular ion: 304.262 (cation), 154.287 (anion).

1,10-Bis(3-methylimidazolium-1-yl)decane dimethionine (IL-12). $C_{28}H_{52}N_6O_4S_2$, MW: 600.882 g/mol; from 4.6 g (10 mmol) of IL-7, and 3.0 g (20 mmol) of L-methionine, 4.8 g of IL-12 was obtained (yield: 80%); $T_g$: 56.42° C.; $^1$H NMR (500 MHz, DMSO-$d_6$): d 9.91 (s, 2H), 7.87 (s, 2H), 7.80 (s, 2H), 4.20 (t, 4H), 3.90 (s, 6H), 2.87 (d, 2H, methionine), 2.48 (m, 4H, methionine), 2.00 (s, 6H, methionine), 1.79 (m, 4H), 1.79 (t, 2H, methionine), 1.47 (t, 2H), 1.24 (m, 12H). $^{13}$C NMR (125 MHz, DMSO-$d_6$): d 176.21 (2C, methionine), 137.05 (2C), 123.36 (2C), 122.04 (2C), 55.18 (2C, methionine), 48.49 (2C), 35.57 (2C, methionine), 35.46 (2C), 30.72 (2C, methionine), 29.27 (2C), 28.56 (2C), 28.19 (2C), 25.34 (2C), 14.52 (2C, methionine). MS m/z molecular ion: 304.262 (cation), 148.236 (anion).

1,8-bis(3-methylimidazolium-1-yl) octane tetrafluorborate (IL-13): $C_{16}H_{28}B_2F_8N_4$, MW: 450.03 g/mol; MP: 73.5° C.; $T_g$: −37.5° C.; $^1$H NMR (400 MHz, DMSO): δ 9.08 (s, 2H), 7.74 (s, 2H), 7.69 (s, 2H), 4.14 (t, 4H), 3.85 (s, 6H), 1.77 (qui, 4H), 1.27 (m, 8H). $^{13}$C NMR (100.32 MHz, DMSO): δ 136.4 (2 C), 123.6 (2 C), 122.2 (2 C), 48.8 (2 C), 35.7 (2 C), 29.3 (2 C), 28.1 (2 C), 25.4 (2 C). MS m/z molecular ion ($M^+$): 363.

1,8-bis(3-methylimidazolium-1-yl)octane bis (trifluoromethane) sulfonimide (IL-14): $C_{20}H_{28}F_{12}N_6O_8S_4$, MW: 836.71 g/mol; $T_g$: −61.4° C.; $^1$H NMR (400 MHz, D2O): δ 9.08 (s, 2H), 7.74 (s, 2H), 7.69 (s, 2H), 4.16 (t, 4H), 3.87 (s, 6H), 1.80 (qui, 4H), 1.30 (m, 8H). $^{13}$C NMR (100.32 MHz, DMSO): δ 136.3 (2 CH), 123.4 (2 CH), 122.1 (2 C), 48.7 (2 C), 35.5 (2 C), 29.1 (2 C), 27.9 (2 C), 25.3 (2 C). MS m/z molecular ion ($M^+$):556.1.

3. Toxicity of the Ionic Liquids

Without wishing to be bound by any theory, it is believed that the ionic liquids (ILs) structures prevent the hydrophobic effects of the imidazolium cation and thus cellular uptake by the introduction of a second cationic head. These structures, which are formed by two imidazolium rings linked by an alkyl chain and anionic counterpart, may result in non-toxic compounds because the dicationic structure will not be able to penetrate and alter the physical properties of the lipid bilayer. The ionic liquids were synthesized and performed preliminary studies with the dicationic imidazolium-based IL compounds as described above, and the $IC_{50}$ values were assessed through MTT assay (Gindri et al., 2014). The results (Table 5) were shown to be from 3 to 20-fold higher than the value observed for a monocationic IL analogous to IL1 ([$C_8$mim][Br]), which $IC_{50}$ was 1.51±0.2 (Gindri et al., 2014; Cvjetko et al., 2012; García-Lorenzo et al., 2008 and Radošević et al., 2013). According to Radosevic et al. (Radošević et al., 2013), ILs with $IC_{50}$ from 0.1 mM to 5 mM are classified as moderately toxic, while ILs with $IC_{50}$ values higher than 5 mM possess low toxicity

TABLE 5

Toxicity ($IC_{50}$) for designed ILs towards MC3T3-E1 cell line.[a]

| IL | $IC_{50}$ (mM) |
|---|---|
| IL1 | 24.6 ± 3.5 |
| IL2 | 3.6 ± 0.6 |
| IL3 | 8.3 ± 3.0 |
| IL4 | 12.5 ± 0.2 |
| IL5 | 25.7 ± 8.7 |
| IL6 | 24.2 ± 10.3 |
| IL7 | 12.3 ± 0.1 |
| IL8 | 3.1 ± 1.2 |
| IL9 | 8.5 ± 1.5 |
| IL10 | 12.3 ± 0.5 |
| IL11 | 12.9 ± 1.1 |
| IL12 | 13.9 ± 2.7 |

[a]Ionic liquid structures shown in Table 4.

Example 2

Biocompatibility

Assays have been performed in a few studies to characterize the toxicity and biodegradability of several imidazolium ionic liquids in aqueous environments. Romero et al. (2008) found that the shorter the chain length of side chains, the lower the toxicity effects of such ionic liquids. Contrary, the anion has been observed to have very little effect on ionic liquids toxicity (Romero et al., 2008; Bernot et al., 2005). Therefore, toxicity of ionic liquids may be attributed to the alkyl chain of choice. The disclosed ionic liquid structures differ from these compounds as the ionic liquids are dicationic with adjustable alkyl chain length to reduce cellular toxicity. Without being bound by theory, the dicationic with adjustable alkyl chain length is believed to be an important factor for determining toxicity. A microscopic and ellipsometry studies were performed to verify the stability of the proposed ionic liquids in physiological medium. Ionic liquids with anions $Br^-$, $BF_4^-$ and $NTf_2^-$ were prepared and deposited on the surface of $Ti_6Al_4V$ disks, which were allowed to dry. Following drying, the disks were immersed in phosphate buffered saline (PBS) solution for 2 days and were removed for microscopic measurements. Microscopy revealed that the thickness of the film remained unchanged on both materials for the period of time evaluated.

Example 3

Adhesion and IL-substrate Affinity

In order to evaluate the affinity of ionic liquids with the titanium surface, experiments were conducted with imidazole derived ionic liquids having as contra-ion the anions $Br^-$, $BF_4^-$ and $NTf_2^-$. In the study, $TiO_2$ nanoparticles were used instead of bulk titanium in order to allow for a better understanding of the interaction of the selected ionic liquids with the Ti oxide film ($TiO_2$). Thermal behavior of $TiO_2$ pure (nanoparticles), ionic liquid pure and the equimolar mixture of $TiO_2$ and the different ionic liquids attempted were evaluated. The data obtained are summarized in Table 6, from which it can be observed that $TiO_2$ does not show any thermal event in a cycle of heating and cooling. The data in Table 6 suggests that when the $TiO_2$ nanoparticles are mixed with the dicationic ionic liquids provided herein a new crystalline phase is formed. Based upon the loss of a glass transition and the introduction of a new melting point for the $TiO_2$ nanoparticle and the $[DBMIM]_2[NTf_2]$, without wishing to be bound by any theory, it is believed that a more organized structural arrangement is formed (Grindri, et al., 2014).

TABLE 6

Thermal data of pure ionic liquid and mixture of ionic liquid and $TiO_2$[a]

| Thermal Analysis | $TiO_2$ | $[DBMIM]_2[Br]$ (IL-1) | | $[DBMIM]_2[BF_4]$ (IL-13) | | $[DBMIM]_2[NTf_2]$ (IL-14) | |
|---|---|---|---|---|---|---|---|
| | | Pure | IL + $TiO_2$ | Pure | IL + $TiO_2$ | Pure | IL + $TiO_2$ |
| $MP_1$(° C.)[b] | — | 68.4 | 67.4 | 73.5 | 65.2 | — | −29.8 |
| $MP_2$(° C.)[c] | — | 99.2 | 209.4 | — | — | — | — |
| $\Delta H°_{f1}$ (KJ/mol)[d] | — | 18.2 | 38.0 | 22.9 | 32.2 | — | 1.06 |
| $\Delta H°_{f2}$ (KJ/mol)[e] | — | 9.8 | 25.1 | — | — | — | — |
| $T_g$(° C.)[f] | — | — | — | 37.5 | — | −61.4 | −59.7 |
| $T_{d1}$(° C.)[g] | >900 | 307.5 | 310.0 | 346.8 | 343.8 | 473 | 463 |
| $T_{d2}$(° C.)[h] | — | — | 372.9 | 455.8 | 455.8 | — | — |

[a]Ionic liquid structures shown in Table 4
[a]First melting point;
[b]Second melting point;
[c]Fusion entalphy of first melting point;
[d]Fusion entalphy of second melting point;
[e]Glass transition temperature;
[f]First decomposition temperature;
[g]Second decomposition temperature.

To evaluate the morphologic characteristics of new structures formed by $TiO_2$+ionic liquid both DLS and SEM techniques were used. SEM demonstrated that morphological changes occurred when comparing, pure ionic liquids, and pure $TiO_2$ with $TiO_2$+ionic liquid. Coating $TiO_2$ nanoparticles with the ionic liquids resulted in a more aggregate and smooth structure in relation to pure ionic liquids and pure $TiO_2$ particles. DLS experiments were performed with $TiO_2$ particles only, and with solutions of equimolar amounts of $TiO_2$+ionic liquid. The data obtained is summarized in Table 7. The hydrodynamic radius ($R_h$) of pure $TiO_2$ particles and mixture of $TiO_2$+ionic liquid was monitored and compared in order to analyze the formation of new organized phases related to ionic liquid film adhesion on $TiO_2$ particles. Two relaxation modes ($R_{h1}$ and $R_{h2}$) were detected from the DLS analysis, indicating that all systems were polydisperse. The value from the difference between the size of $TiO_2$+ionic liquid and $TiO_2$ was used to calculate ionic liquid film thickness formed on $TiO_2$ particles.

TABLE 7

DLS data of pure ionic liquids and mixture of ionic liquid and $TiO_2$[a]

| DLS | $TiO_2$ | [DBMIM]$_2$[Br] (IL-1) IL + $TiO_2$ | Thickness[b] IL + $TiO_2$ | [DBMIM]$_2$[BF$_4$] (IL-13) IL + $TiO_2$ | Thickness[b] IL + $TiO_2$ | [DBMIM]$_2$[NTf$_2$] (IL-14) IL + $TiO_2$ | Thickness[b] IL + $TiO_2$ |
|---|---|---|---|---|---|---|---|
| $R_{h1}$[b] | 0.6 | 0.8 | 0.2 | 0.7 | 0.1 | 1.6 | 0.9 |
| $R_{h2}$[b] | 303.5 | 421.9 | 118.4 | 513.0 | 209.5 | 894.6 | 591.1 |

[a]Ionic liquid structure shown in Table 4
[b](nm); h1: relaxation mode 1; h2: relaxation mode 2.

Comparing the data between pure $TiO_2$ and the mixtures of [DBMIM]$_2$[Br], [DBMIM]$_2$[BF$_4$] and [DBMIM]$_2$[NTf$_2$], it can be observed that in the first relaxation mode ($Rh_1$) a small difference was detected between the size of the particles, which can be related with the single $TiO_2$ nanoparticles, [DBMIM]$_2$[Br], [DBMIM]$_2$[BF$_4$] and [DBMIM]$_2$[NTf$_2$] dispersed in solution. However, in the second relaxation mode a significant difference was noted between the size of pure $TiO_2$ nanoparticles and $TiO_2$+ionic liquid (Table 6). It was observed that $R_{h2}$ tended to increase with ionic liquid presence, which thus indicates film formation on the particles surface. Another interesting characteristic from the DLS results is that film thickness increased with hydrophobicity of anions (FIG. 1), which is in agreement with the trend reported by Ulbricht and Wittmar, 2012.

Figures 2A, 2B, 2C, 2D, 2E, 2F:
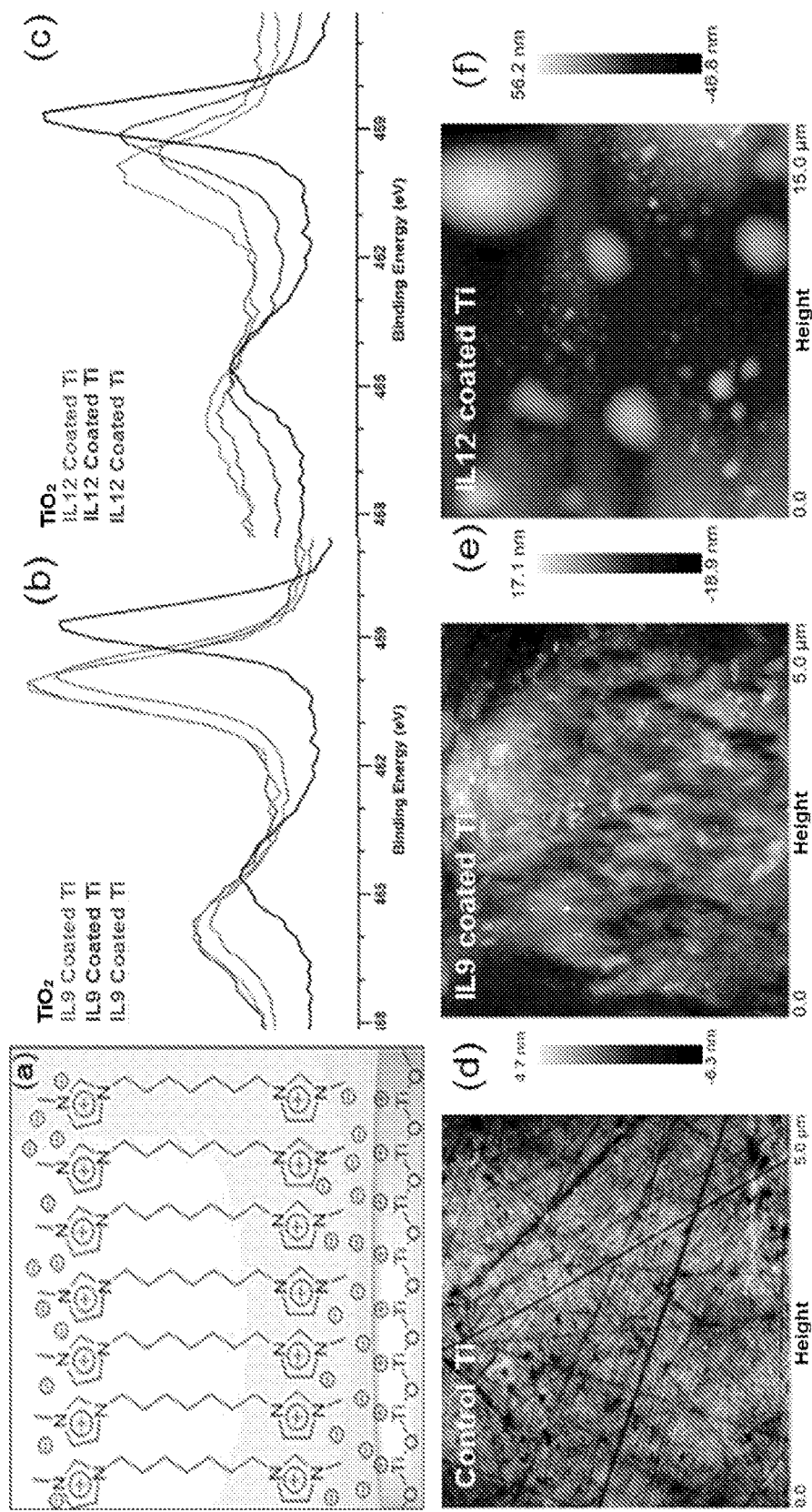
FIGS. 2A-2F show hypothesized structure of IL on TiO$_2$ surface (FIG. 2A). Overlay of Ti Control and (FIG. 2B) IL9 coated Ti and (FIG. 2C) IL12 coated Ti XPS spectra and height profile for (FIG. 2D) Ti Control, (FIG. 2E) IL9 coated Ti and (FIG. 2F) IL12 coated. In both samples, it is possible to observe a variation of BE of Ti 2p on coated samples in relation to the control showing that there is interaction between Ti and ILs.

The mechanism of interaction between charged surface layers and ILs is illustrated in FIG. 2A. It is suggested that dicationic imidazolium ILs work to establish a more robust and dense adsorption film than their monocationic counterparts (Zhou et al., 2009; Jiménez et al., 2010 and Bermúdez et al., 2000). This trend was further investigated using X-ray photoelectron spectroscopy (XPS) and Atomic Force Microscopy (AFM) for IL9-coated Ti and IL12-coated Ti, due to the higher hydrophobicity of IL9 in comparison to IL12. The XPS provided a measurement of binding energy (BE) of each atom on the Ti surface. Comparing these results with the BE of atoms in pure IL and Ti control enabled the understanding of the sites of interaction between coating and substrate. FIG. 2B and FIG. 2C show the Ti 2p spectra of Ti control (black line), and tree different areas (gray lines) on IL9-coated Ti and IL12-coated Ti, respectively. In both samples, it is possible to observe a variation of BE of Ti 2p on coated samples in relation to the control showing that there is interaction between Ti and ILs. FIG. 2B showed that Ti 2p was constant regardless the area analyzed on IL9-coated Ti, demonstrating homogeneous coating profile. On the contrary, Ti 2p BE had different shifts in distinct areas on the surface of IL12-coated Ti revealing heterogeneous coating profile. These findings were further evidenced with AFM images. FIGS. 2D-2F showed the surface morphology of control, IL9-coated Ti and IL12-coated Ti, respectively. It is possible to observe that IL9, which is more hydrophobic, covered the entire surface of Ti while IL12 formed aggregates. These preliminary results demonstrated that ILs adhere on Ti surfaces forming films with morphology and thicknesses adjustable by the degree of IL compound hydrophobicity.

Example 5

Lubrication and Corrosion Activity

The proposed mechanism of interaction with a charged surface, such as the surface of biomedical alloys, is illustrated in FIG. 2A. The electronic structure of titanium and its oxide layer plays a key role in the interaction between the oxide containing surface and other materials. The charges of ionic liquid compounds can be adjusted to have tuned interactions with the charged substrate. For example, $Ti^+$ on the oxide surface acts as Lewis acids, accepting electrons. Whereas, O atoms are basic sites interacting with electron acceptors ($H^+$ protons) and creating bridging hydroxyls. Therefore, the electronic structure of the surface will drive the design of ionic liquids to maximize interactions and increase adhesion strength. These compounds will form thin films on the surface, which can be deposited by using simple dip coating.

Figure 3:
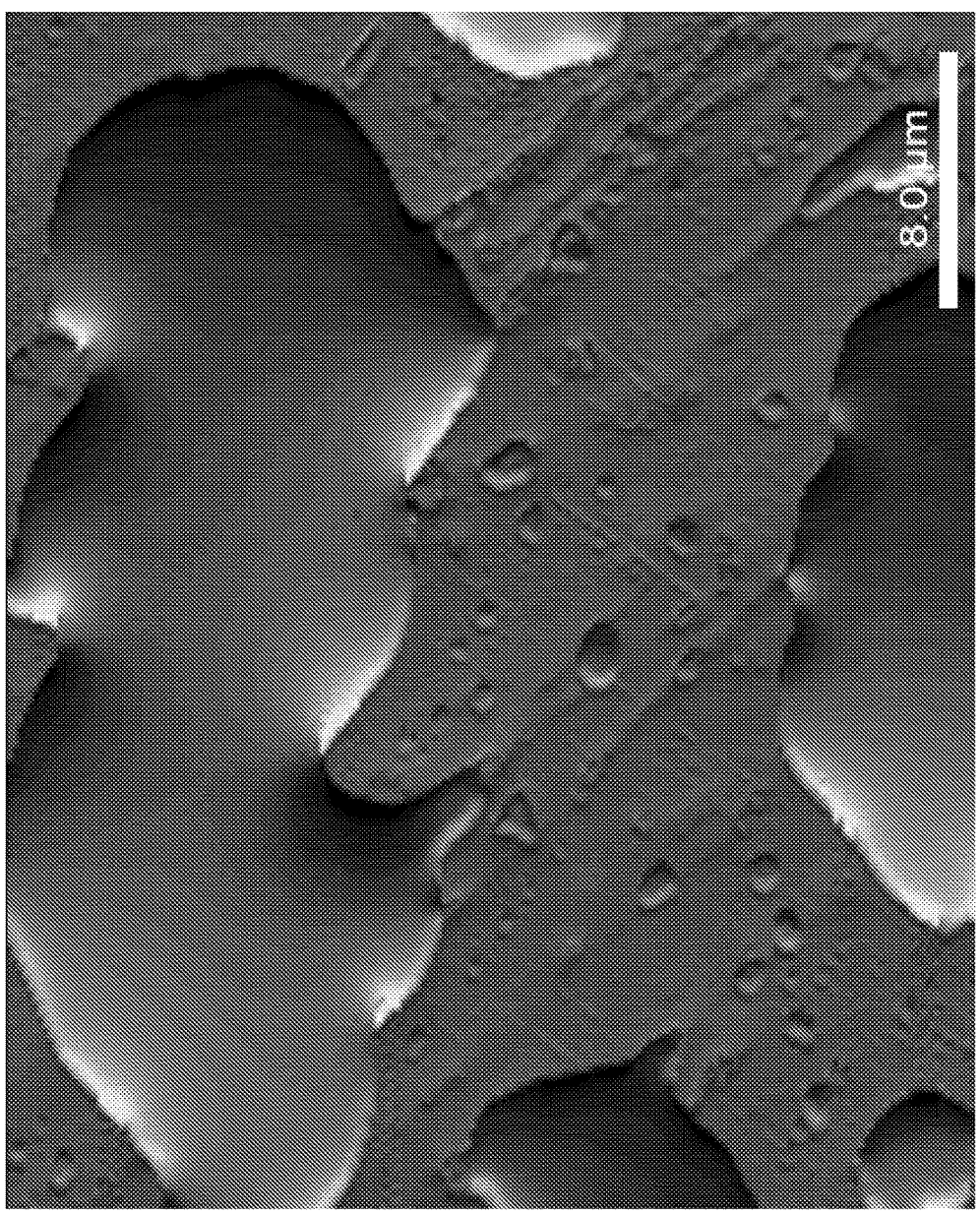
FIG. 3 shows the AFM of bulk titanium treated with ionic liquids. Coating was performed following a non-controlled dipping process, which explains the non-uniform droplets present on the surface. This compound had no pharmaceutical component in its formulation, so it was only meant to confer better friction (lubrication) properties to the surface.

The thickness of the film depends of the hydrophobicity degree of the compound synthesized. Atomic Force Microscopy (AFM) confirmed film formation on the surface of bulk titanium, as illustrated in FIGS. 2 and 3. Results showed that IL9 was also able to lubricate the surface and reduce the friction coefficient to 0.1, while IL12 provided only a little lubrication. The lubrication provided by IL9 was maintained during the entire experiment without losing its properties, showing high coating stability simulating 1 day of mastication. See FIG. 4D.

Figures 4A, 4B, 4C, 4D, 4E:
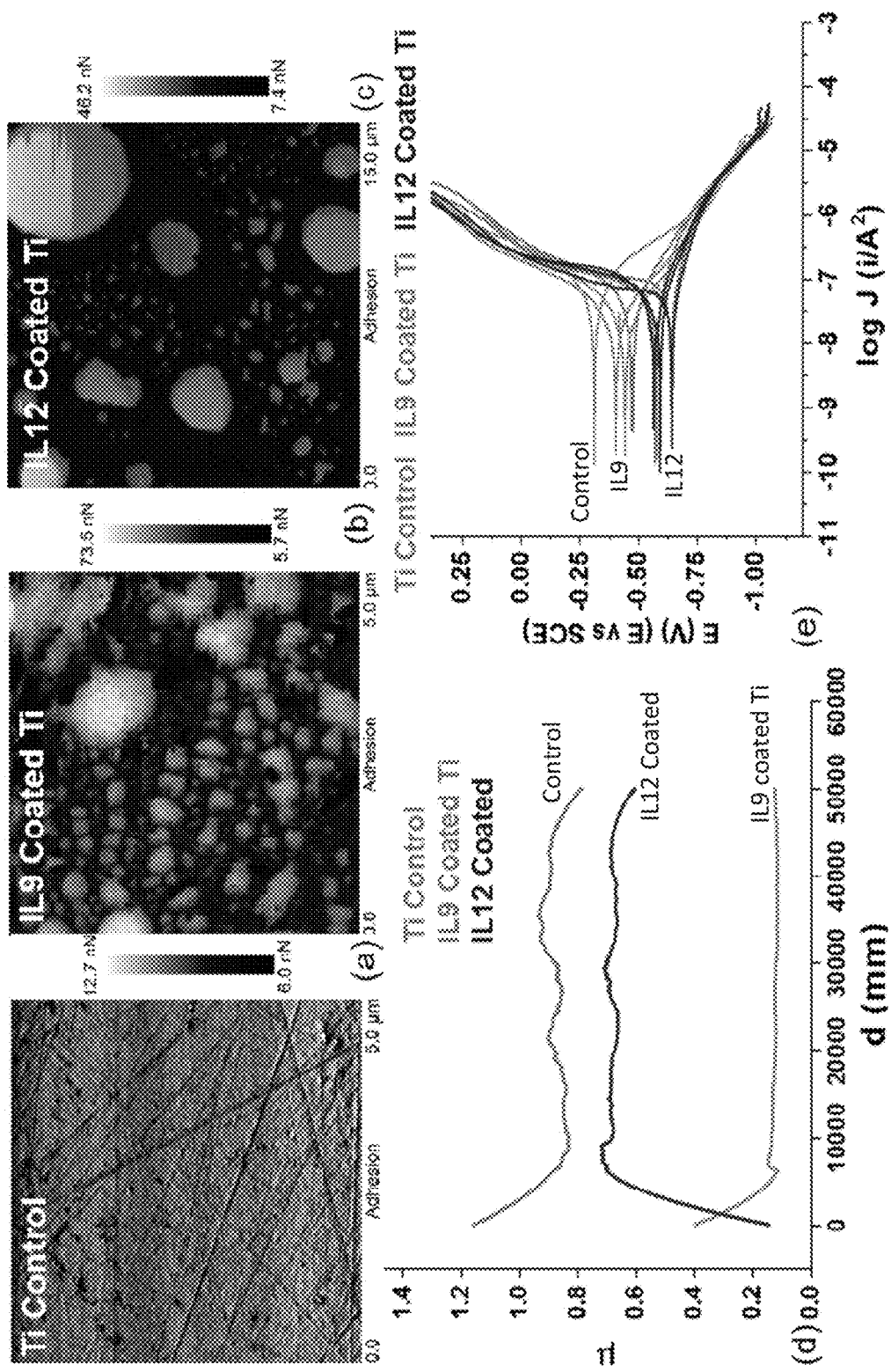
FIGS. 4A-4E show adhesion strength of (FIG. 4A) Ti control, (FIG. 4B) IL9-coated Ti and (FIG. 4C) IL12-coated Ti.

Zhou et al. related the superior lubricant activity of ILs, compared with conventional fluids, to their high polarity and ability to form strong adsorption films on different substrates (Zhou et al., 2009). Preliminary investigation of the performance of two ILs (IL9 and IL12) coated Ti surfaces demonstrated promising results in regards to coating stability, lubrication and anti-corrosive activities. As shown in FIGS. 4A-4C, the adhesion force on coated surfaces was also dependent on IL hydrophobicity. For the IL9-coated Ti surfaces coating adhesion strength values were around 73.5 nN, while IL12-coated Ti showed lower adhesion strength (46.2 nN). These results demonstrate that besides improved coating performance, the more hydrophobic IL9 interacted stronger with the Ti surface.

These ionic liquids were further investigated with electrochemical experiments to explore the anti-corrosive property of these two compounds (Table 8). IL12 showed similar corrosion resistance. However, IL9 had improved results showing higher stability, demonstrated by high open circuit potentials (OCP), the IL improved the corrosion resistance, which was reflected by higher $E_{corr}$ (corrosion potential) and lower $I_{corr}$ (corrosion current) values in comparison to the Ti control.

TABLE 8

Electrochemical parameters for control and coated samples.[a]

| Sample | OCP | $E_{corr}$ | $I_{corr}$ | Corrosion Rate |
|---|---|---|---|---|
| Control | −0.24.6 ± 0.02 | −0.56 ± 0.08 | 4.7 × 10$^{-8}$ ± 1.7 × 10$^{-8}$ | 4.1 × 10$^{-4}$ ± 1.5 × 10$^{-4}$ |

TABLE 8-continued

Electrochemical parameters for control and coated samples.[a]

| Sample | OCP | $E_{corr}$ | $I_{corr}$ | Corrosion Rate |
|---|---|---|---|---|
| IL9 | −0.15 ± 0.02 | −0.38 ± 0.07 | $2.0 \times 10^{-8} \pm 9.2 \times 10^{-9}$ | $1.7 \times 10^{-4} \pm 8.0 \times 10^{-5}$ |
| IL12 | −0.24 ± 0.02 | −0.60 ± 0.04 | $4.0 \times 10^{-8} \pm 2.7 \times 10^{-9}$ | $3.5 \times 10^{-4} \pm 2.3 \times 10^{-5}$ |

[a]Ionic liquid structures shown in Table 4.

Example 6

Host Cell Activity

The ionic liquids were synthesized and performed preliminary studies with the dicationic imidazolium-based IL compounds as described above, and the $IC_{50}$ values were assessed through MTT assay (Egorova et al., 2014). The toxicity of ionic liquids was accessed using MC3T3-E1 cell lines. The cells were plated in 6-well plates and after 24 h, cells were treated with media containing a range of concentrations of ionic liquids. All concentrations tested for generation of dose-response curves. A non-linear regression sigmoidal dose-response curve was fitted to each set of values to allow the calculation of $IC_{50}$ values. The results (Table 5) were shown to be from 3 to 20-fold higher than the value observed for a monocationic IL analogous to IL1 ([$C_8$mim][Br]), which $IC_{50}$ was 1.51±0.2 (Gindri et al., 2014; Cvjetko et al., 2012; García-Lorenzo et al., 2008 and Radošević et al., 2013). According to Radosevic et al. (Radošević et al., 2013), ILs with $IC_{50}$ from 0.1 mM to 5 mM are classified as moderately toxic, while ILs with $IC_{50}$ values higher than 5 mM possess low toxicity. Additionally toxicity data is also shown in FIG. 5.

Figures 6A, 6B, 6C, 6D, 6E, 6F:
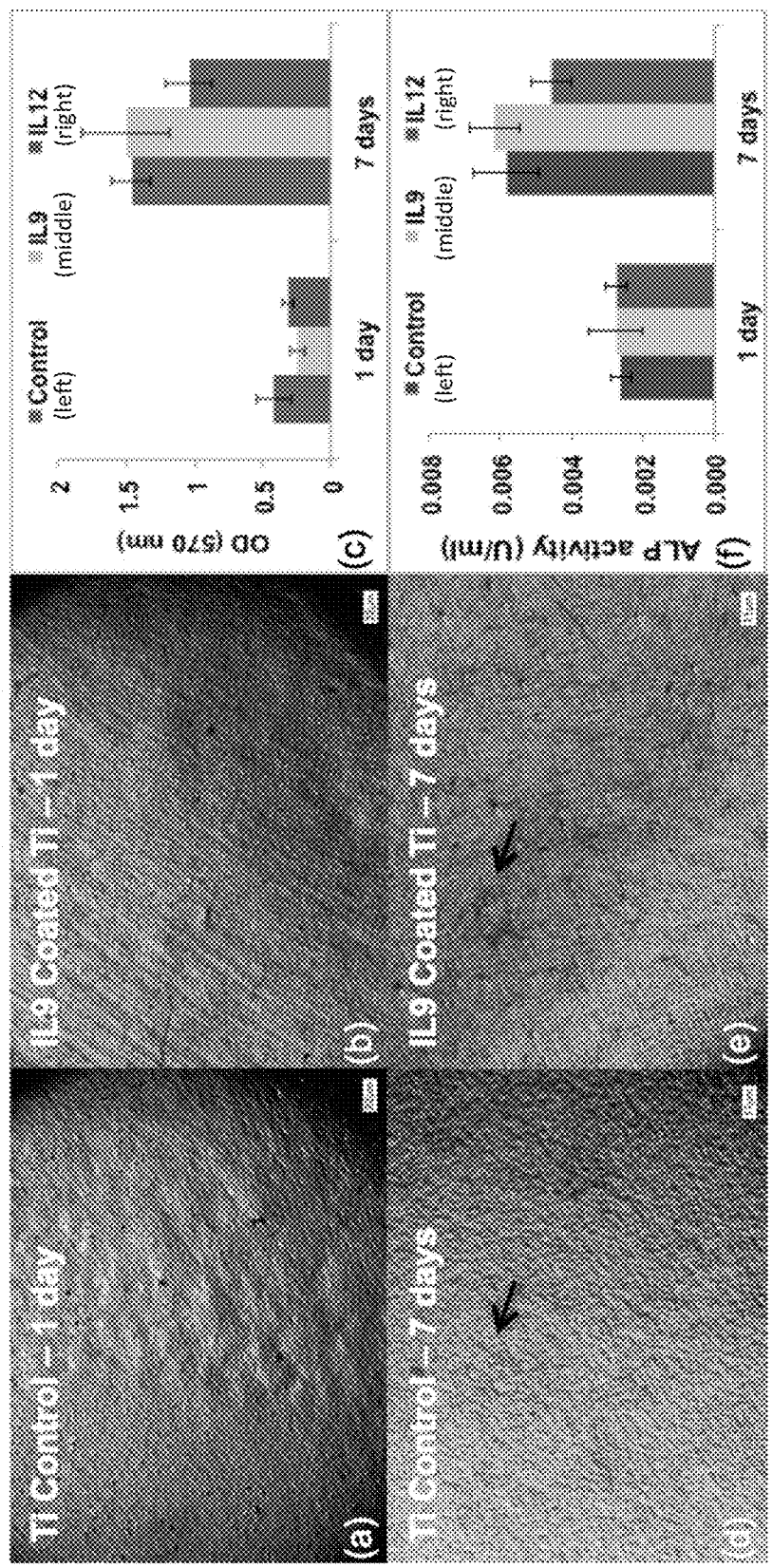
FIGS. 6A-6F show osteoblast identification through alkaline phosphatase assay. Ti Control on day 1 (FIG. 6A) and day 7 (FIG. 6D) along with IL9 coated Ti shown on day 1 (FIG. 6B) and day 7 (FIG. 6E) are shown.

Experiments were performed in which Ti control disks, IL9-coated Ti, and IL12-coated Ti were exposed to gingival epithelial (HGF-1) and osteoblast-like cells (MC3T3-E1) during periods of 1 and 7 days. It was observed that after 1 day both Ti control and IL-coated Ti were covered with a layer of osteoblast-like cells (FIGS. 6A & 6B) illustrating the initial cell attachment on the surface. The cell proliferation for both cell lines, assessed through MTT assay, did not show significant differences between Ti control and IL9-coated Ti as illustrated for osteoblast-like cells after 1 (FIGS. 6A & 6B) and 7 days (FIGS. 6D & 6E). In vitro and in vivo osteoblast cell differentiation can be characterized during a phase denominated matrix maturation. During this period, a high expression of alkaline phosphatase (AP) is observed and can be used as an early differentiation marker to evaluate the differentiation of stem cells into osteoblasts (Shang et al., 2014 and Wang et al., 2012). The ALP activity was measured on both time points and it was observed that both coated and control samples allowed for cell differentiation without statistically significant differences (p<0.05) (compare FIG. 6C to FIG. 6F). Cell differentiation was observed after 7 days on Ti control and IL9 coated Ti in which osteoblast are distinguished from stem cells by the purple color of the stain as indicated by the black arrows (FIGS. 6D & 6E).

Example 7

Antimicrobial Activity

Figure 7:
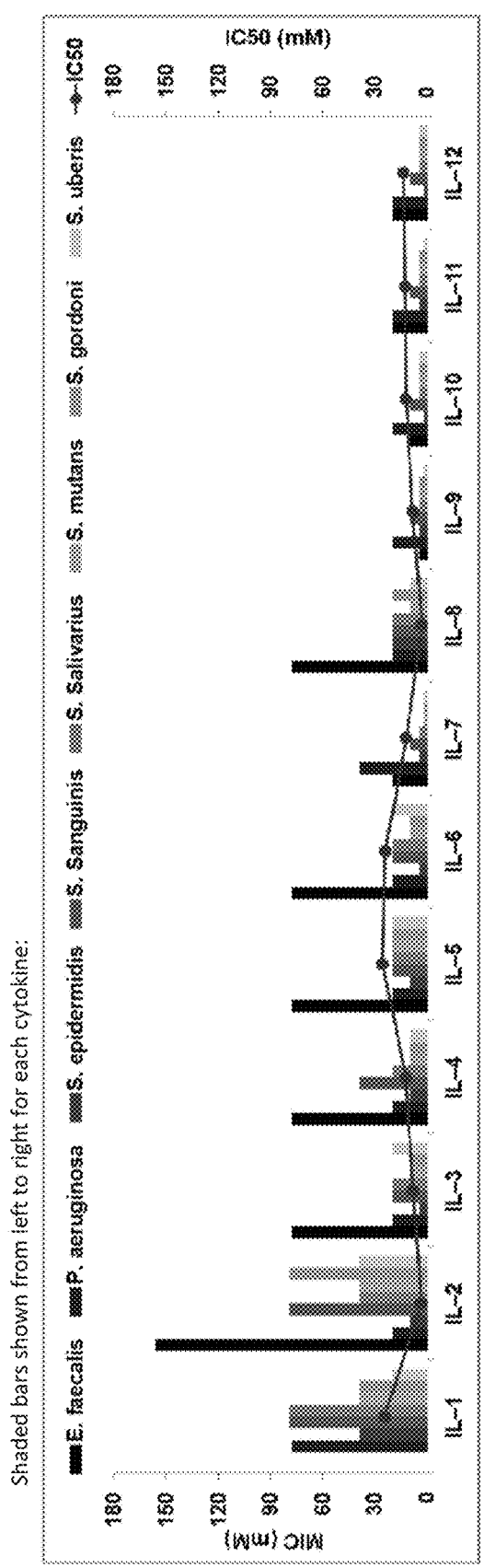
FIG. 7 shows the comparison IC$_{50}$ and MIC (Gindri et al., 2014). The IC$_{50}$ is shown by the line and the bars show the minimum inhibitory concentration (MIC) for eight different bacterial strains. The bacterial strains are *Pseudomonas aeruginosa* PA14, *Enterococcus faecalis* V583, *Staphylococcus epidermidis*, *Streptococcus mutans* UA159, *Streptococcus salivarius* 13419, *Streptococcus sanguinis* 10556, *Streptococcus gordonii* DL1.1, and *Streptococcus uberis* 13419. The best results were found for IL9-IL12, which exhibited lower MIC values with high IC$_{50}$.

The antimicrobial activity of the IL compounds was also investigated against a panel of bacterial strains with clinical relevance for human oral infections as well as other infection sites (FIG. 7) (*Pseudomonas aeruginosa* PA14, *Enterococcus faecalis* V583, *Staphylococcus epidermidis*, *Streptococcus mutans* UA159, *Streptococcus salivarius* 13419, *Streptococcus sanguinis* 10556, *Streptococcus gordonii* DL1.1, and *Streptococcus uberis* 13419) (Gindri et al., 2014; Gindri et al., 2014; Nováková et al., 2013; Dahlén et al., 2012; Albertini et al., 2014 and Sievert et al., 2013). Except for *P. aeruginosa*, which is gram-negative, all of these are gram-positive bacteria. MIC values were determined using broth microdilution (Gindri et al., 2014) and results are illustrated in FIG. 7. Most of the ILs investigated inhibited bacterial growth. An increase in IL alkyl chain length resulted in an increase in antimicrobial activity. FIG. 7 shows the correlation between MIC and $IC_{50}$ results. A conflict between cytotoxicity and antimicrobial activity did not occur for some of the ILs tested, particularly when considering bacterial species relevant to the oral environment. When the red line (corresponding to $IC_{50}$ values) is above MIC bars, the IL can be considered a strong candidate for biological applications with regards to the bacterial strains used in the preliminary investigation. The best results were found for IL9-IL12, which exhibited lower MIC values with high $IC_{50}$. The selective toxicity against bacteria is likely due to differences in membrane phospholipid composition and cell surface chemistry between bacterial and eukaryotic (host cell) membranes. Therefore, these compounds appear to be suitable for coating of Ti surfaces.

Figure 8:
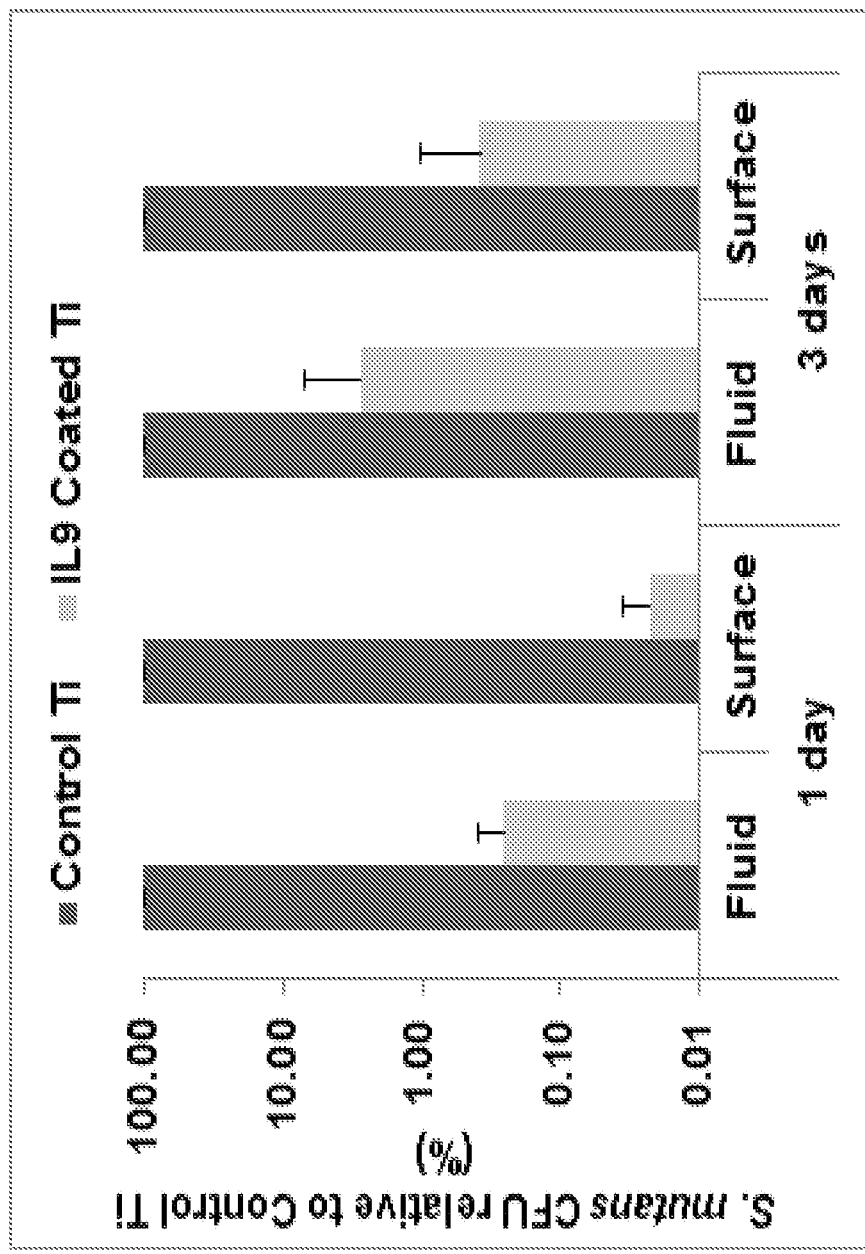
FIG. 8 shows the percentage of reduction of *S. mutans* on IL-9 Coated Ti in relation to the Ti Control in the fluid medium, and on samples surfaces. On average, ~10$^6$ colony forming units (CFU) *S. mutans* were attached to control Ti surfaces after 24 h. In comparison, only ~10$^2$ CFU were recovered from IL9-coated Ti surfaces after 24 h (expressed as a percent CFU reduction relative to control in FIG. 12). Data from a 72 h trial show that IL9-coated surfaces retain significant anti-*S. mutans* activity with longer incubation.

To determine if ILs retain antimicrobial activity when applied to Ti, preliminary experiments with two ILs (IL9 and IL12) and *S. mutans*, an early colonizer. Control Ti, IL9-coated Ti, and IL12-coated Ti were immersed in artificial saliva/brain heart infusion (BHI) medium containing *S. mutans* for 24 h and 72 h. After this period, planktonic bacterial cells in the fluid medium in which disks were immersed, and biofilm cells, adhered to the disk surface, were quantified by serial dilution and plating. IL12-coated Ti did not show significant antimicrobial activity. Data for control and IL9-coated Ti are shown in FIG. 12 and discussed further here. On average, ~$10^6$ colony forming units (CFU) *S. mutans* were attached to control Ti surfaces after 24 h. In comparison, only ~$10^2$ CFU were recovered from IL9-coated Ti surfaces after 24 h (expressed as a percent CFU reduction relative to control in FIG. 8). Data from a 72 h trial show that IL9-coated surfaces retain significant anti-*S. mutans* activity with longer incubation (FIG. 8). These data demonstrate that IL9-coated Ti has significant antibiofilm activity against an early colonizer over a period of one week, mimicking the critical initial healing period.

* * *

All of the compositions and methods disclosed and claimed herein can be made and executed without undue experimentation in light of the present disclosure. While the compositions and methods of this invention have been described in terms of certain embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 6,039,568
U.S. Pat. No. 8,075,312
U.S. Patent Application No. 2005/0037319
U.S. Patent Application No. 2012/0077151
Albertini et al., Clin. Oral Implants Res., 00:1-5, 2014.
Bermúdez et al., Molecules, 14:2888-2908, 2000.
Bernot et al., Environ. Toxicol. Chem., 24:87-92, 2005.
Heidelberg, Germany, Second Edition, 2008.
New York, Second Edition, 1996.
Cheng, et al., *Journal of Biomedical Materials Research Part A*, 2013 in press.
Chin et al., Biomaterials, 28:2032-2040, 2007.
Clyne et al., *Biomaterials*, 1998; 19:2015-2029.
Collier et al., *Clinical orthopedics*, 1991; 271:305-312.
Cvjetko et al., Arh. Hig. Rada Toksikol., 63:15-20, 2012.
Dahlén et al., J. Oral Microbiol., 4:1-7, 2012.
Davis, *Nature Reviews Drug Discovery*, 2003; 2:114-122.
Egorova et al., Chem Sus Chem 7:336-360, 2014.
Ferris, et al., *Biomaterials*, 1999; 20:2323-2331.
Frizzo et al., Pharmaceutical salts: solids to liquids by using ionic liquid design. Pharmaceutical Salts: Solids to Liquids by Using Ionic Liquid Design. 1 ed.: Intech, v.1, p. 557-579, 2013.
Fukumoto et al., *Journal of American Chemical Society*, 127:2398-2399, 2005.
García-Lorenzo et al., Green Chem., 10:508, 2008.
Gibson and Stamn, *Business briefing: medical device manufacturing & technology*, 48-51, 2002.
Gilbert and Jacobs, ASTM STP 1301, 157-176, 1997.
Gilbert et al., *Journal of Biomedical Materials Research*, 27:1533-1544, 1993.
Gindri et al., ACS Appl. Mater. Interfaces, 6:11536-11543, 2014.
Gindri et al., RSC Adv., 4:62594-62602, 2014.
Gindri, et al., *ACS Applied Materials & Interfaces*, 2014.
Goldberg and Gilbert, *Biomaterials*, 25:851-864, 2004.
Goldberg et al., *Clinical Orthopedics and Related Research*, 401:149-161, 2002.
Gordon et al., *Journal of Materials Chemistry*, 8:2627, 1998.
Hendry and Pilliar, *Journal of Biomedical Materials Research Part B: Applied Biomaterials*, 58(1):156-166, 2001.
Jacobs et al., *Journal of Bone and Joint Surgery*, 80(2): 268-282, 1998.
Jiménez et al., Tribol. Lett., 40:237-246, 2010.
Koike et al., Biomaterials, 22:2931-2936, 2001.
Liu et al., *Chemical Society Reviews*, 38:2590-2599, 2009.
Liu et al., *Tribology Letters*, 13(2):81-85, 2002.
Mathew et al., J. Biomed. Mater. Res. B. Appl. Biomater., 100:1662-1671, 2012.
Minami, *Molecules*, 14:2286-2305, 2009.
Narbat, et al., *Journal of Biomedical Materials Research Part B*, 100B:1344-1352, 2012.
Nováková et al., Folia Microbiol. (Praha)., 58:649-656, 2013.
Palacio and Bushan, *Advanced Materials*, 10:1194-1198, 2008.
Pradier, et al., *Accounts of Chemical Research*, 43(10): 1297-1306, 2012.
Quirynen & van Steenberghe, *Clinical Oral Implants Research*, 4:158-161, 1993.
Quirynen, et al., *Clinical Oral Implants Research*, 13: 1-19, 2002.
Radošević et al., Ecotoxicol. Environ. Saf., 92:112-118, 2013.
Renvert et al., *Clinical Oral Implantology Research*, 18:509-516, 2007.
Rodrigues et al., Dent. Mater., (under rev), 2015.
Rodrigues et al., J. Biomed. Mater. Res. B. Appl. Biomater., 88:206-219, 2009.
Rodrigues et al., *Journal of Biomedical Materials Research Part B: Applied Biomaterials*, 88(1):206-219, 2009.
Rodrigues et al., Materials (Basel), 6:5258-5274, 2013.
Romero et al., J. Hazard. Mater., 151:268-273, 2008.
Sánchez et al., Dent. Mater., 30:1161-1171, 2014.
Shang et al., Int. J. Oral Sci., 1-8, 2014.
Sievert et al., Infect Control Hosp Epidemiol., 34:1-14, 2013.
Simchi, et al., *Nanomedicine: Manotechnology, Biology and Medicine*, 7:22-39, 2011.
Streicher, *Journal of Arthroplasty*, 13(3) 343-345, 1998.
Svensson et al., Nanomedicine, 9:1048-1056, 2013.
Tillander, et al., *Clinical Orthopedics Related and Research*, 468:2781-2788, 2010.
Tsuchiya et al., J. Orthop. Sci., 17:595-604, 2012.
Ulbricht and Wittmar, *Industrial & Engineering Chemistry Research*, 51:8425-8433, 2012.
Vargas-Reus et al., Int. J. Antimicrob. Agents, 40:135-139, 2012.
Wang et al., Biomed. Pharmacother., 66:633-641, 2012.
Wang, et al., *Annual Academy Medical Singapore*, 40:237-244, 2011.
Weber and Cochran, J. Prosthet. Dent., 79:79-89, 1989.
Wilson et al., J Periodontol., 86:9-15, 2015.
Wilson et al., J. Periodontol., 85:657-660, 2014.
Wittmar et al., Ind. Eng. Chem. Res., 51:8425-8433, 2012.
Zemmerli, *Best Practice & Research Clinical Rheumatology*, 20(6): 1045-1063, 2006.
Zhao et al., Dent. Mater., 30:716-727, 2014.
Zhou et al., Chem. Soc. Rev., 38:2590-2599, 2009.

What is claimed is:

1. A method of using an ionic liquid comprising a cation of the formula:

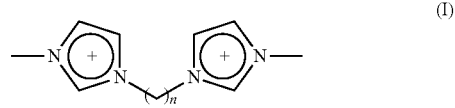

(I)

wherein:
n is 2-16;
an anion selected from:
a β-lactam compound, an amino acid$_{(C \leq 18)}$; phosphate, alkylphosphate$_{(C \leq 12)}$, substituted alkylphosphate$_{(C \leq 12)}$, dialkylphosphate$_{(C \leq 12)}$, substituted dialkylphosphate$_{(C \leq 12)}$, a sugar, ascorbic acid, $B(Y_1)(Y_2)(Y_3)(Y_4)^-$ wherein $Y_1$, $Y_2$, $Y_3$, and $Y_4$ are each independently selected from halogen; hydroxyl; amino; alkyl$_{(C\le6)}$; alkenyl$_{(C\le6)}$; alkynyl$_{(C\le6)}$; aryl$_{(C\le12)}$; aralkyl$_{(C\le12)}$; acyl$_{(C\le6)}$; alkoxy$_{(C\le6)}$; aryloxy$_{(C\le12)}$; acyloxy$_{(C\le6)}$; or a substituted version of any of the last nine groups, halide, and $N(A_1)(A_2)^-$ wherein:

$A_1$ and $A_2$ are each independently selected from alkyl$_{(C\le12)}$, substituted alkyl$_{(C\le12)}$, cycloalkyl$_{(C\le12)}$, substituted cycloalkyl$_{(C\le12)}$, alkylsulfonyl$_{(C\le12)}$, substituted alkylsulfonyl$_{(C\le12)}$, cycloalkylsulfonyl$_{(C\le12)}$, or substituted cycloalkylsulfonyl$_{(C\le12)}$;

wherein the method comprises depositing the ionic liquid on any surface of an implantable device.

2. The method of claim 1, wherein the cation is further defined by the formula:

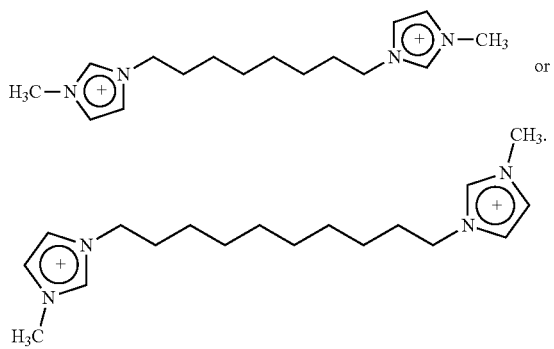

or

3. The method of claim 1, wherein the anion is an amino acid$_{(C\le12)}$.

4. The method of claim 1, wherein the anion is phosphate.

5. The method of claim 1, wherein the anion is $B(Y_1)(Y_2)(Y_3)(Y_4)^-$, wherein $Y_1$, $Y_2$, $Y_3$, and $Y_4$ are each independently selected from halogen, hydroxyl, amino, alkyl$_{(C\le6)}$, alkenyl$_{(C\le6)}$, alkynyl$_{(C\le6)}$, aryl$_{(C\le12)}$, aralkyl$_{(C\le12)}$, acyl$_{(C\le6)}$, alkoxy$_{(C\le6)}$, aryloxy$_{(C\le12)}$, acyloxy$_{(C\le6)}$, or a substituted version of any of these groups.

6. The method of claim 5, wherein $Y_1$, $Y_2$, $Y_3$, and/or $Y_4$ is halogen.

7. The method of claim 1, wherein the anion is ascorbic acid.

8. The method of claim 1, wherein the anion is $N(A_1)(A_2)^-$.

9. The method of claim 1, wherein the anion is a β-lactam compound.

10. The method of claim 9, wherein the β-lactam compound is a β-lactam antibiotic.

11. The method of claim 1, further comprising:
(a) a cation of the formula:

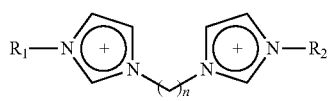

(III)

wherein:
$R_1$ and $R_2$ are alkyl$_{(C\le8)}$ or substituted alkyl$_{(C\le12)}$; and
n is 2-16; and
(b) an anion selected from an amino acid$_{(C\le18)}$, sugar, and ascorbic acid.

12. The method of claim 1, wherein the device is a medical device.

* * * * *